United States Patent
Luttrull et al.

(10) Patent No.: US 10,357,398 B2
(45) Date of Patent: Jul. 23, 2019

(54) SYSTEM AND PROCESS FOR TREATMENT OF MYOPIA

(71) Applicant: Ojai Retinal Technology, LLC, Ojai, CA (US)

(72) Inventors: Jeffrey K. Luttrull, Ojai, CA (US); David B. Chang, Tustin, CA (US); Benjamin W. L. Margolis, Oakland, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 21 days.

(21) Appl. No.: 15/813,645

(22) Filed: Nov. 15, 2017

(65) Prior Publication Data
US 2018/0078412 A1 Mar. 22, 2018

Related U.S. Application Data

(60) Division of application No. 15/629,002, filed on Jun. 21, 2017, now Pat. No. 10,278,863, which is a
(Continued)

(51) Int. Cl.
*A61F 9/008* (2006.01)
*A61F 9/007* (2006.01)
(Continued)

(52) U.S. Cl.
CPC .............. *A61F 9/008* (2013.01); *A61B 18/20* (2013.01); *A61B 90/36* (2016.02); *A61F 9/007* (2013.01);
(Continued)

(58) Field of Classification Search
CPC .......... A61F 9/008; A61F 9/007; A61B 18/20; A61N 5/06
(Continued)

(56) References Cited

U.S. PATENT DOCUMENTS 3,408,593 A 10/1968 Hurwitz, Jr.
4,048,011 A 9/1977 Kovin et al.
(Continued)

FOREIGN PATENT DOCUMENTS

DE 10 2010 022 760 A1 12/2011
WO 2006005038 A2 1/2006
(Continued)

OTHER PUBLICATIONS

Du et al, Heat shock protein 70 expression induced by diode laser irradiation on choroid-retinal endothelial cells in vitro, vol. 18, Sep. 21, 2012, pp. 2380-2387 [online], [retrieved on Aug. 5, 2018]. Retreived from the Internet <URL: http://www.molvis.org/molvis/v18/a251>.*
(Continued)

*Primary Examiner* — Gary Jackson
*Assistant Examiner* — Sebastian X Lukjan
(74) *Attorney, Agent, or Firm* — Kelly & Kelley, LLP

(57) ABSTRACT

A process for preventing or treating myopia includes applying a pulsed energy, such as a pulsed laser beam, to tissue of an eye having myopia or a risk of having myopia. The source of pulsed energy has energy parameters including wavelength or frequency, duty cycle and pulse train duration, which are selected so as to raise an eye tissue temperature up to eleven degrees Celsius to achieve therapeutic or prophylactic effect, such as stimulating heat shock protein activation in the eye tissue. The average temperature rise of the eye tissue over several minutes is maintained at or below a predetermined level so as not to permanently damage the eye tissue.

25 Claims, 14 Drawing Sheets

Related U.S. Application Data continuation-in-part of application No. 15/583,096, filed on May 1, 2017, now abandoned, and a continuation-in-part of application No. 15/460,821, filed on Mar. 16, 2017, and a continuation-in-part of application No. 15/332,132, filed on Oct. 24, 2016, now Pat. No. 10,117,777, and a continuation-in-part of application No. 15/291,796, filed on Oct. 12, 2016, now Pat. No. 10,285,859, and a continuation-in-part of application No. 15/232,320, filed on Aug. 9, 2016, now Pat. No. 9,962,291, and a continuation-in-part of application No. 15/214,726, filed on Jul. 20, 2016, and a continuation-in-part of application No. 15/188,608, filed on Jun. 21, 2016, now Pat. No. 10,238,542, and a continuation-in-part of application No. 15/148,842, filed on May 6, 2016, and a continuation-in-part of application No. 15/075,432, filed on Mar. 21, 2016.

(51) Int. Cl.

| | | |
|---|---|---|
| *A61N 5/02* | (2006.01) | |
| *A61N 5/04* | (2006.01) | |
| *A61N 5/06* | (2006.01) | |
| *A61N 7/00* | (2006.01) | |
| *A61B 18/20* | (2006.01) | |
| *A61B 90/00* | (2016.01) | |
| *A61B 17/00* | (2006.01) | |
| *A61B 18/00* | (2006.01) | |
| *A61N 5/067* | (2006.01) | |

(52) U.S. Cl.
CPC .......... *A61F 9/00821* (2013.01); *A61N 5/025* (2013.01); *A61N 5/045* (2013.01); *A61N 5/06* (2013.01); *A61N 5/0603* (2013.01); *A61N 5/0625* (2013.01); *A61N 7/00* (2013.01); *A61B 17/00* (2013.01); *A61B 2017/00061* (2013.01); *A61B 2018/00589* (2013.01); *A61B 2090/3735* (2016.02); *A61F 9/00817* (2013.01); *A61F 2009/00863* (2013.01); *A61F 2009/00872* (2013.01); *A61N 5/0622* (2013.01); *A61N 2005/063* (2013.01); *A61N 2005/0604* (2013.01); *A61N 2005/0607* (2013.01); *A61N 2005/067* (2013.01); *A61N 2005/0608* (2013.01); *A61N 2005/0609* (2013.01); *A61N 2005/0659* (2013.01); *A61N 2005/0662* (2013.01); *A61N 2007/0004* (2013.01); *A61N 2007/0043* (2013.01)

(58) Field of Classification Search
USPC .......................................................... 606/5
See application file for complete search history.

(56) References Cited

U.S. PATENT DOCUMENTS

| | | | |
|---|---|---|---|
| 4,176,325 A | 11/1979 | Kajimura et al. | |
| 4,194,114 A | 3/1980 | Pankratov et al. | |
| 4,410,365 A | 10/1983 | Glukhovsky et al. | |
| 4,695,733 A | 9/1987 | Pesavento | |
| 4,730,335 A | 3/1988 | Clark et al. | |
| 4,791,634 A | 12/1988 | Miyake | |
| 4,825,880 A | 5/1989 | Stauffer et al. | |
| 4,865,029 A | 9/1989 | Pankratov et al. | |
| 4,879,722 A | 11/1989 | Dixon et al. | |
| 4,930,504 A | 6/1990 | Diamantopoulos et al. | |
| 4,933,944 A | 6/1990 | McGraw | |
| 4,935,931 A | 6/1990 | McGraw | |
| 4,961,079 A | 10/1990 | Owens et al. | |
| 4,967,416 A | 10/1990 | Esterowitz et al. | |
| 5,037,421 A | 8/1991 | Boutacoff et al. | |
| 5,067,951 A | 11/1991 | Greve | |
| 5,085,492 A | 2/1992 | Kelsoe et al. | |
| 5,088,803 A | 2/1992 | Buzawa | |
| 5,147,354 A | 9/1992 | Boutacoff et al. | |
| 5,372,595 A | 12/1994 | Gaasterland et al. | |
| 5,394,199 A | 2/1995 | Flower | |
| 5,430,756 A | 7/1995 | Hanihara | |
| 5,520,680 A | 5/1996 | Shapshay et al. | |
| 5,651,019 A | 7/1997 | Goldberg et al. | |
| 5,982,789 A | 11/1999 | Marshall et al. | |
| 6,050,990 A | 4/2000 | Tankovich et al. | |
| 6,066,128 A | 5/2000 | Bahmanyar et al. | |
| 6,129,722 A * | 10/2000 | Ruiz ..................... | A61F 9/008 351/212 |
| 6,156,028 A | 12/2000 | Prescott | |
| 6,208,769 B1 | 3/2001 | Pankratov | |
| 6,222,869 B1 | 4/2001 | Marshall et al. | |
| 6,259,952 B1 | 7/2001 | Sluijter et al. | |
| 6,327,291 B1 | 12/2001 | Marshall | |
| 6,377,599 B1 | 4/2002 | Marshall | |
| 6,540,391 B2 | 4/2003 | Lanzetta et al. | |
| 6,681,185 B1 | 1/2004 | Young et al. | |
| 6,715,877 B2 | 4/2004 | Molebny | |
| 6,733,490 B1 | 5/2004 | Falsini et al. | |
| 6,813,942 B1 | 11/2004 | Vozhdaev et al. | |
| 6,889,695 B2 | 5/2005 | Pankratov et al. | |
| 6,942,655 B2 | 9/2005 | Peyman | |
| 7,227,196 B2 | 6/2007 | Burgener, II et al. | |
| 7,229,435 B2 | 6/2007 | Nakamura | |
| 7,387,785 B1 | 6/2008 | Rudin et al. | |
| 7,452,081 B2 | 11/2008 | Wiltberger et al. | |
| 7,645,276 B2 | 1/2010 | Pankratov et al. | |
| 7,763,828 B2 | 7/2010 | Talwar et al. | |
| 7,766,903 B2 | 8/2010 | Blumenkranz et al. | |
| 7,766,904 B2 | 8/2010 | McGowan, Sr. et al. | |
| 7,771,417 B2 | 8/2010 | Telfair et al. | |
| 7,909,816 B2 | 3/2011 | Buzawa | |
| 8,454,161 B2 | 6/2013 | Su et al. | |
| 2002/0099363 A1 | 7/2002 | Woodward et al. | |
| 2002/0120255 A1 | 8/2002 | Sotiropoulos et al. | |
| 2002/0165525 A1 | 11/2002 | Nakamura | |
| 2003/0078567 A1 | 4/2003 | Dorin et al. | |
| 2004/0098070 A1 | 5/2004 | Mohr et al. | |
| 2005/0069531 A1 | 3/2005 | Karageozian et al. | |
| 2005/0176662 A1 | 8/2005 | Inana et al. | |
| 2007/0173793 A1 | 7/2007 | Rathjen | |
| 2007/0213693 A1 | 9/2007 | Plunkett | |
| 2008/0015553 A1 | 1/2008 | Zacharias | |
| 2008/0058783 A1* | 3/2008 | Altshuler ............. | A61B 18/203 606/9 |
| 2008/0076958 A1 | 3/2008 | Britva et al. | |
| 2009/0093798 A1 | 4/2009 | Charles | |
| 2009/0198309 A1* | 8/2009 | Gowda ............... | A61B 18/1815 607/102 |
| 2010/0049180 A1* | 2/2010 | Wells ................... | A61N 5/0616 606/12 |
| 2010/0068141 A1 | 3/2010 | Kaushal et al. | |
| 2010/0082024 A1 | 4/2010 | Brannan et al. | |
| 2010/0152716 A1 | 6/2010 | Previn et al. | |
| 2010/0168724 A1 | 7/2010 | Sramek et al. | |
| 2010/0249760 A1 | 9/2010 | Blumenkranz et al. | |
| 2010/0290007 A1 | 11/2010 | Van de Velde | |
| 2011/0196350 A1 | 8/2011 | Friedman et al. | |
| 2011/0306956 A1* | 12/2011 | Islam ................... | A61B 18/20 606/15 |
| 2013/0116672 A1 | 5/2013 | Yee | |
| 2013/0231721 A1 | 9/2013 | DeCharms | |
| 2013/0317487 A1 | 11/2013 | Luttrull et al. | |
| 2013/0317570 A1 | 11/2013 | Luttrull et al. | |
| 2014/0121631 A1 | 5/2014 | Bean et al. | |
| 2014/0228824 A1 | 8/2014 | Yee et al. | |
| 2016/0296374 A1 | 10/2016 | Luttrull et al. | |

(56) References Cited

U.S. PATENT DOCUMENTS

| | | | |
|---|---|---|---|
| 2016/0338757 A1 | 11/2016 | Luttrull et al. | |
| 2016/0346126 A1 | 12/2016 | Luttrull et al. | |
| 2016/0361572 A1 | 12/2016 | Slayton | |

FOREIGN PATENT DOCUMENTS

| | | | |
|---|---|---|---|
| WO | 2007035855 A2 | 3/2007 | |
| WO | 2007106521 A2 | 9/2007 | |
| WO | 2011/050056 A2 | 4/2011 | |

OTHER PUBLICATIONS

Sramek et al, Non-damaging Retinal Phototherapy: Dynamic Range of Heat Shock Protein Expression. Investigative Ophthalmology & Visual Science, vol. 52, No. 3, Mar. 28, 2011, pp. 1780-1787 [online], [retrieved on Aug. 6, 2018]. Retrieved from the Internet <URL: https://iovs.arvojournals.org/article.aspx?articleid=2127223>.*

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

Luttrull et al. Subthreshold diode micropulse panretinal photocoagulation for proliferative diabetic retinopathy. Eye (2007), 1-6 © 2007 Nature Publishing Group, www.nature.com/eye.

Small Beam Diameter Scanning Galvo Mirror Systems; Thorlabs; 1999-2013, 4 pgs.

Keller, Matthew D. et al.; Raman Spectroscopy for Cancer Diagnosis; www.spectroscopyonline.com; Nov. 2006 21(11); pp. 33-41 (including Reference (21) thereof).

International Search Report for PCT/US2015/0060836 dated Jan. 29, 2016.

Allingham RR, Damji KF, Freedman S, et al. Shields Textbook of Glaucoma, 6th Ed., 2010, Wolters Kluwer / Lippincott Williams & Wilkins, Philadelphia. ISBN-13: 978-0-7817-9585-2.

Danesh-Meyer HV, Levin LA. Glaucoma as a neurodegenerative disease. J Neuroophthalmol. Sep. 2015; 35 Suppl 1: S22-8.

Tian K, Shibata-Germanos S, Pahlitzsch M, Cordeiro Mf. Current perspective of neuroprotection and glaucoma. Clin Ophthalmol. Nov. 11, 2015; 9: 2109-18.

Vujosevic S, Boffega E, Casciano M, et al. Microperimetry and fundus autofluorescence in diabetic macular edema. Subthreshold micropulse diode laser versus modified Early Treatment Diabetic Retinopathy Study Laser photocoagulation. Retina 2010; 30:908-16.

Lavinsky D, Cardillo JA, Melo, et al. Randomized clinical trial evaluating mETDRS versus normal or high-density micropulsephotocoagulation for diabetic macular edema. Invest Ophthalmol Vis Sci. Jun. 17, 2011; 52 (7): 4314-23.

Luttrull JK, Spink CJ, Musch DA. Subthreshold diode micropulse panretinal photocoagulation for proliferative diabetic retinopathy. Eye, May 2008; 22 (5): 607-12.

Luttrull JK, Sramek C, Palanker D, Spink CJ, Musch DC. Long-term safety, high-resolution imaging, and tissue temperature modeling of subvisible diode micropulse photocoagulation for retinovascular macular edema. Retina 2012; 32 (2): 375-86.

Malik KJ1, Sampat KM, Mansouri A, Steiner JN, Glaser BM. Low-intensity/high-density subthreshold microPulse diode laser for chronic central serous chorioretinopathy. Retina. Mar. 2015;35(3):532-6.

Luttrull, JK. Subthreshold diode micropulse laser (SDM) for central serous chorioretinopathy. Retina, Jan. 2016 (in press).

Luttrull JK, Donn G. Subthreshold diode micropulse photocoagulation as invisible retinal phototherapy for diabetic macular edema. A review. Current Diabetes Reviews, 2012, 8, 274-284.

Luttrull JK, Chang DB, Margolis BWL, Darin G, Luttrull DK. Laser re-sensitization of medically unresponsive-neovascular age-related macular degeneration: Efficacy and implications. Retina Jun. 2015; 35(6): 1184-1194.

Luttrull JK, Margolis BWL. Functionally guided retinal protective therapy as prophylaxis for age-related and inherited retinal degenerations. A pilot study. Invest Ophthalmol Vis Sci. Jan. 1, 2016;57(1):265-75. doi: 10.1167/iovs.15-18163.

McCulloch DL, Marmor MF, Brigell MG, et al. ISCEV Standard for full-field clinical electroretinography (2015 update). Doc Ophthalmol. Feb. 2015; 130 (1): 1-12.

Porciatti V, Ventura LM. Normative Data for a User-friendly Paradigm for Pattern Electroretinogram Recording. Ophthalmology, 2004; 111(1): 161-168.

Gutstein W, Sinclair SH, Presti P, North RV. Interactive thresholding of central acuity under contrast and luminance conditions mimicking real world environments: 1. Evaluation against LogMAR charts. J Comput Sci Sys Bio, 20125; 8(4) 225-232.

Parisi V, Centofanti M, Ziccardi L, et al. Treatment with citicoline drops enhances retinal function and neural conduction along the visual pathways in open angle glaucoma. Graefes Arch Clin Exp Ophthamol, May 2015; DOI 10.1007/s00417-015-3044-9.

Miller NR, ed. Walsh and Hoyt's Clinical Neurophthalmology. 4th Ed, 1985; Chapter 3: 41-60.Williams and Wilkins, Baltimore Maryland.

Salomão SR, Berezovsky A, Andrade RE, et al. Visual electrophysiologic findings in patients from an extensive Brazilian family with Leber'shereditary optic neuropathy. Doc Ophthalmol. Mar. 2004;108(2):147-55.

Kolomeyer AM, Zarbin MA. Trophic factors in the pathogenesis and therapy for retinal degenerative diseases. Surv Ophthalmol. Mar.-Apr. 2014;59 (2):134-65.

Kenealey J, Subramanian P, Comitato A, et al. Small Retinoprotective Peptides Reveal a Receptor-binding Region on Pigment Epithelium-derived Factor. J Biol Chem. Oct. 16, 2015;290(42):25241-53.

Yu PK1, Cringle SJ, McAllister IL, Yu DY. Low power laser treatment of the retina ameliorates neovascularisation in a transgenic mouse model of retinalneovascularisation. Exp Eye Res. Nov. 2009;89(5):791-800.

Flaxel C1, Bradle J, Acott T, Samples Jr. Retinal pigment epithelium produces matrix metalloproteinases after laser treatment. Retina. Jun. 2007;27 (5):629-34.

Sramek C, Mackanos M, Spitler R, et al. Non-damaging retinal phototherapy: dynamic range of heat shock protein expression. Invest Ophthalmol Vis Sci. Mar. 28, 2011; 52 (3):1780-7.

Ventura LM, Feuer WJ, Porciafti V. Progressive loss of retinal ganglion cell function is hindered with IOP-lowering treatment in early glaucoma. IOVS, Feb. 2012 53 (2): 659-663.

Ventura LM, Porciafti V. Restoration of retinal ganglion cell function in early glaucoma after intraocular pressure reduction. A pilot study. Ophthalmology 2005, 112 (1): 20-27.

Yap GH, Chen LY, Png R, et al. Clinical value of electrophysiology in determining the diagnosis of visual dysfunction in neuro-ophthalmology patients. Doc Ophthalmol. Dec. 2015;131(3):189-96.

Waisbourd M, Ahmed Om, Molineaux J, et al. Reversible structural and functional changes after intraocular pressure reduction in patients with glaucoma. Graefes Arch Clin Exp Ophthalmol. Mar. 19, 2016. [Epub ahead of print] PMID: 26995555.

Banitt MR, Ventura LM, Feuer WJ, Savatovsky E, et al. Progressive loss of retinal ganglion cell function precedes structural loss by several years in glaucoma suspects. IOVS, Mar. 2013; 54 (3): 2346-2352.

(56) References Cited

OTHER PUBLICATIONS

Karu T. Photobiology of low-power laser effects. Review. Health Phys. May 1989; 56 (5): 691-704.
Gao X, Xing D. Molecular mechanisms of cell proliferation induced by low power laser irradiation. J Biomed Sci. Jan. 12, 2009;16:4.
Dorin G, Luttrull JK, Samples JR. Chapter 21: Laser alteration of collector channel ostia. Pivotal paradigm shift from photocoagulation to photostimulation. Glaucoma Research and Clinical Advances: 2016 to 2018. Knepper and Samples, Eds. Kugler Pub. Jan. 1, 2016, Amsterdam, Netherlands. ISBN: 9789062992478.
Van Teijlingen Eri, Rennie Am, Hundley V, Graham W. The importance of conducting and reporting pilot studies: the example of the Scottish Births Survey. J Adv Nurs. May 2001; 34 (3): 289-95.
Luttrull JK, Sinclair SH. Safety of transfoveal subthreshold diode micropulse laser (SDM) for fovea-involving diabetic macular edema in eyes with good visual acuity. Retina. Oct. 2014; 34 (10): 2010-20.
Luttrull, JK and Margolis BWL. improved retinal function following SDM laser for chronic disease. American Society of Retina Specialists Annual Meeting Vienna, Austria. Jul. 11, 2015 [online]. [retrieved on Jan. 11, 2017] <URL: http://www.diopsys.com/wp-content/uploads/2015/07/Luttrutl_Improved-retinal-function-following-SDM-laser-for-chronic-disease_ASRS2015.pdf>.
International Search Report for the International application No. PCT/US2016/46043 dated Dec. 27, 2016.
International Search Report for International Application No. PCT/US2016/62421 dated Feb. 7, 2017.
International Search Report for the International Application No. PCT/US2018/042833 dated Sep. 21, 2018.

\* cited by examiner

SYSTEM AND PROCESS FOR TREATMENT OF MYOPIA

RELATED APPLICATIONS

This application is a divisional of U.S. patent application Ser. No. 15/629,002, filed Jun. 21, 2017, which is a continuation-in-part of U.S. application Ser. No. 15/583,096 filed May 1, 2017, which is a continuation-in-part of U.S. application Ser. No. 15/214,726 filed on Jul. 20, 2016, which is a continuation-in-part of U.S. application Ser. No. 14/922,885 filed on Oct. 26, 2015 (now U.S. Pat. No. 9,427,602) (which claims priority from U.S. Provisional Application No. 62/153,616 filed on Apr. 28, 2015), which is a continuation-in-part of U.S. application Ser. No. 14/607,959 filed on Jan. 28, 2015 (now U.S. Pat. No. 9,168,174), which is a continuation-in-part of U.S. application Ser. No. 13/798,523 filed on Mar. 13, 2013, which is a continuation-in-part of U.S. application Ser. No. 13/481,124 filed on May 25, 2012 (now U.S. Pat. No. 9,381,115), and is also a continuation-in-part of U.S. application Ser. No. 15/232,320 filed on Aug. 9, 2016, which is a continuation-in-part of U.S. application Ser. No. 15/188,608 filed Jun. 21, 2016, which is a continuation-in-part of U.S. application Ser. No. 15/148,842 filed on May 6, 2016, which is a continuation-in-part of U.S. application Ser. No. 14/921,890 filed Oct. 23, 2015 (now U.S. Pat. No. 9,381,116), which is a continuation-in-part of U.S. application Ser. No. 14/607,959 filed Jan. 28, 2015 (now U.S. Pat. No. 9,168,174). This application is also a continuation-in-part of U.S. application Ser. No. 15/460,821 filed Mar. 16, 2017, which is a continuation-in-part of U.S. application Ser. No. 15/214,726, filed Jul. 20, 2016, which is a continuation-in-part of U.S. application Ser. No. 14/922,885, filed on Oct. 26, 2015, now U.S. Pat. No. 9,427,602 (which claims the benefit of U.S. Application No. 62/153,616, filed on Apr. 28, 2015), which is a continuation-in-part of U.S. application Ser. No. 14/607,959 filed on Jan. 28, 2015, now U.S. Pat. No. 9,168,174, which is a continuation-in-part of U.S. application Ser. No. 13/798,523, filed on Mar. 13, 2013, which is a continuation-in-part of U.S. application Ser. No. 13/481,124, filed on May 25, 2012, now U.S. Pat. No. 9,381,115, and is also a continuation-in-part of U.S. application Ser. No. 15/148,842, filed May 6, 2016, which is a continuation-in-part of U.S. application Ser. No. 14/921,890, filed Oct. 23, 2015, now U.S. Pat. No. 9,381,116, which is a continuation-in-part of U.S. application Ser. No. 14/607,959, filed on Jan. 28, 2015, now U.S. Pat. No. 9,168,174, which is a continuation-in-part of U.S. application Ser. No. 13/798,523, filed Mar. 13, 2013, which is a continuation-in-part of U.S. application Ser. No. 13/481,124, filed on May 25, 2012, now U.S. Pat. No. 9,381,115; and also a continuation-in-part of U.S. application Ser. No. 15/075,432, filed on Mar. 21, 2016, which is a continuation of U.S. application Ser. No. 13/798,523, filed on Mar. 13, 2013, which is a continuation-in-part of U.S. application Ser. No. 13/481,124, filed May 25, 2012, now U.S. Pat. No. 9,381,115. This application is also a continuation-in-part of U.S. application Ser. No. 15/332,132 filed Oct. 24, 2016, which is a divisional of U.S. application Ser. No. 15/232,320, filed Aug. 9, 2016, which is a continuation-in-part of U.S. application Ser. No. 15/148,842, filed May 6, 2016 which is a continuation-in-part of U.S. application Ser. No. 14/921,890, filed Oct. 23, 2015 (now U.S. Pat. No. 9,381,116), which is a continuation-in-part of U.S. application Ser. No. 14/607,959 filed Jan. 28, 2015 (now U.S. Pat. No. 9,168,174), which is a continuation-in-part of U.S. application Ser. No. 13/798,523, filed Mar. 13, 2013, which is a continuation-in-part of U.S. application Ser. No. 13/481,124, filed May 25, 2012 (now U.S. Pat. No. 9,381,115); and is also a continuation-in-part of U.S. application Ser. No. 15/188,608, filed Jun. 21, 2016, which is a continuation of U.S. application Ser. No. 13/481,124, filed May 25, 2012 (now U.S. Pat. No. 9,381,115); and is a continuation-in-part of U.S. application Ser. No. 13/798,523, filed Mar. 13, 2013, which is a continuation-in-part of U.S. application Ser. No. 13/481,124, filed May 25, 2012 (now U.S. Pat. No. 9,381,115). This application is also a continuation-in-part of U.S. application Ser. No. 15/291,796 filed Oct. 12, 2016 which is a divisional of U.S. Ser. No. 15/148,842, filed May 6, 2016, which is a continuation-in-part of U.S. application Ser. No. 14/921,890, filed Oct. 23, 2015, which is a continuation-in-part of U.S. application Ser. No. 14/607,959, filed Jan. 28, 2015 (now U.S. Pat. No. 9,168,174), which is a continuation-in-part of U.S. application Ser. No. 13/798,523, filed Mar. 13, 2013, which is a continuation-in-part of U.S. application Ser. No. 13/481,124, filed May 25, 2012; and is also a continuation-in-part of U.S. application Ser. No. 15/075,432, filed Mar. 21, 2016, which is a continuation of U.S. application Ser. No. 13/798,523, filed Mar. 13, 2013, which is a continuation-in-part of U.S. application Ser. No. 13/481,124, filed May 25, 2012. This application is also a continuation-in-part of U.S. application Ser. No. 15/232,320 filed Aug. 9, 2016 which is a continuation-in-part of U.S. application Ser. No. 15/148,842, filed May 6, 2016 which is a continuation-in-part of U.S. application Ser. No. 14/921,890, filed Oct. 23, 2015 (now U.S. Pat. No. 9,381,116), which is a continuation-in-part of U.S. application Ser. No. 14/607,959, filed Jan. 28, 2015 (now U.S. Pat. No. 9,168,174), which is a continuation-in-part of U.S. application Ser. No. 13/798,523, filed Mar. 13, 2013, which is a continuation-in-part of U.S. application Ser. No. 13/481,124, filed May 25, 2012 (now U.S. Pat. No. 9,381,115); and is also a continuation-in-part of U.S. application Ser. No. 15/188,608, filed Jun. 21, 2016, which is a continuation of U.S. application Ser. No. 13/481,124, filed May 25, 2012 (now U.S. Pat. No. 9,381,115); and is a continuation-in-part of U.S. application Ser. No. 13/798,523, filed Mar. 13, 2013, which is a continuation-in-part of U.S. application Ser. No. 13/481,124, filed May 25, 2012 (now U.S. Pat. No. 9,381,115). This application is also a continuation-in-part of U.S. application Ser. No. 15/214,726 filed Jul. 20, 2016 which is a continuation-in-part of U.S. application Ser. No. 14/922,885, filed on Oct. 26, 2015 (which claims the benefit of U.S. Application No. 62/153,616, filed on Apr. 28, 2015), which is a continuation-in-part of U.S. application Ser. No. 14/607,959 filed on Jan. 28, 2015, now U.S. Pat. No. 9,168,174, which is a continuation-in-part of U.S. application Ser. No. 13/798,523, filed on Mar. 13, 2013, which is a continuation-in-part of U.S. application Ser. No. 13/481,124, filed on May 25, 2012, now U.S. Pat. No. 9,381,115. This application is also a continuation-in-part of U.S. application Ser. No. 15/188,608 filed Jun. 21, 2016 which is a continuation of U.S. application Ser. No. 13/481,124 filed May 25, 2012. This application is also a continuation-in-part of U.S. application Ser. No. 15/148,842 filed May 6, 2016 which is a continuation-in-part of U.S. application Ser. No. 14/921,890, filed Oct. 23, 2015, which is a continuation-in-part of U.S. application Ser. No. 14/607,959, filed Jan. 28, 2015 (now U.S. Pat. No. 9,168,174), which is a continuation-in-part of U.S. application Ser. No. 13/798,523, filed Mar. 13, 2013, which is a continuation-in-part of U.S. application Ser. No. 13/481,124, filed May 25, 2012; and is also a continuation-in-part of U.S. application Ser. No. 15/075,432, filed Mar. 21, 2016, which is a continuation of U.S. application Ser. No. 13/798, 523, filed Mar. 13, 2013, which is a continuation-in-part of U.S. application Ser. No. 13/481,124, filed May 25, 2012. This application is also a continuation-in-part of U.S. application Ser. No. 15/075,432 filed Mar. 21, 2016 which is a continuation of U.S. application Ser. No. 13/798,523, filed Mar. 13, 2013, which is a Continuation-in-Part of U.S. application Ser. No. 13/481,124, filed May 25, 2012.

BACKGROUND OF THE INVENTION

The present invention generally relates to systems and processes for treating eye disorders. More particularly, the present invention resides in systems and processes for preventing or treating myopia by applying pulsed energy to tissue of an eye having myopia or a risk of having myopia to raise the temperature of the eye tissue sufficiently to provide treatment benefits while not permanently damaging the eye tissue.

Myopia is the condition known as "near-sightedness", where the image in front of the eye is focused in front of the retina rather than exactly on the retina. This focus of the image on the retina is also referred to as "emmetropia". The image in myopia may be focused in front of the retina for one or both of the following reasons: either the refractive strength of the front of the eye at the cornea and lens is excessive; and/or the axial length of the eye is too long, such that the retina is posterior to the image focal point, causing blurred vision. To counteract this visual blurring, those affected move closer to the object to be viewed. This moves the focal point of the image back and closer to the retina, causing the vision to become more clear.

Myopia is epidemic by usual medical definitions, affecting as many as 50% of adults, with increases in incidents in school-aged children in recent generations by 200% or more. This rapid increase and prevalence has been attributed to improved educational opportunities with increased reading time, as well as increased use of electronic devices and media.

The causes of typical myopia appear to be genetic and environment. Higher education and greater time spent doing close work and reading are known to be risk factors for myopia. The stimulus for near work causing myopia suggests that this influences, possibly in part via accommodation of the crystalline lens, neurologic and/or chemical mediators of eye growth to increase the axial length of the eye. Evidence for this phenomenon is that paralyzation of accommodation with topical atropine in children is able to reduce the degree and incidence of acquired myopia.

The "emmetropic" factor or factors that promote normal eye growth and formation and axial length and that are diminished, blocked or inhibited by near work lead to an increase in eye length, most likely arise in the central retina or "macula" where visual images are normally focused. By hard-wired neurologic and/or diffusible chemical feedback mechanisms, auto regulation of ocular growth is disturbed to adapt the eye to the myopic focal point by encouraging actively, or allowing passively by loss of emmetropic stimulus, an increase in the axial length of the eye, increasing the condition of myopia.

Retinal dysfunction and alteration of retinal autoregulation in response to environmental factors is a common phenomenon and a common finding in most chronic progressive retinopathies, including age-related macular degeneration and diabetic retinopathy, ocular neurologic diseases such as chronic open angle glaucoma, and inherited retinopathies including retinitis pigmentosa and Stargardt's Disease. In glaucoma a setting analogous to the development of myopia, selective complimentary sparing of visual field defects has demonstrated direct and neurologic and/or chemical communication between fellow eyes mediated by the central nervous system to minimize total visual disability. In response to high eye pressure in glaucoma, optic nerve tissue is sacrificed in such a way as to increase the probability of preserved visual field in one eye, covering lost visual field in the other eye, maximizing total visual function when both eyes are used together. Thus, there is a clear anatomic response mediated by retinal signaling which alters retinal and neurologic structure to accommodate the quality of visual stimuli and maximize visual function.

Pediatric myopic appears to develop and progress in the same manner and by similar mechanisms as other chronic progressive ocular diseases. An abnormal stimulus (chronic near-work and lens accommodation) causing alteration of retinal function and autoregulation in response to the abnormal environment, thus becomes abnormal and causes elongative growth to the eye to restore sharp near vision with less accommodative effort, and thus the condition of myopia develops.

While typical axial or refractive myopia can be corrected by glasses, contact lenses or refractive surgery, myopia is also often associated with reduced visual function and increases risks of vision loss due to retinal detachment, choroidal neovascularization, macular atrophy, and glaucoma. Together, the need for refractive correction of myopia, and medical consequences, constitute a significant public health problem and socioeconomic burden.

Accordingly, there is a continuing need for systems and methods which can prevent and/or treat the eye condition of myopia. Such a system or method should be able to modify biological factors that may contribute to acquired myopia, so as to slow or prevent acquired myopia. Such a system and method of treatment should be relatively easy to perform and harmless. The present invention fulfills these needs, and provides other related advantages.

SUMMARY OF THE INVENTION

The present invention resides in a process for preventing or treating myopia. A pulsed energy source having energy parameters, including wavelength or frequency, duty cycle and pulse duration is provided. The energy parameters are selected so as to raise an eye tissue temperature up to 11° C. to achieve a therapeutic or prophylactic effect. The average temperature rise of the eye tissue over several minutes is maintained at or below a predetermined level so as not to permanently damage the eye tissue. It may be determined that the eye has myopia or is at a risk of having myopia. The pulsed energy is applied to tissue of an eye having a myopia or a risk of having myopia to stimulate heat shock protein activation in the eye tissue.

The pulsed energy may comprise a pulsed light beam having a wavelength between 530 nm to 1300 nm, and more particularly between 80 nm and 1000 nm. The light beam may have a duty cycle of less than 10%, and more preferably between 2.0% and 5%. The pulsed light beam may have a power between 0.5 and 74 watts. The pulsed light beam may have a pulse train duration between 0.1 and 0.6 seconds.

Typically, the eye tissue to which the pulsed energy is applied comprises retinal and/or foveal tissue. The pulsed energy source energy parameters are selected so that the eye tissue temperature is raised between 6° C. to 11° C. at least during application of the pulsed energy source. However, the average temperature rise of the eye tissue is maintained at approximately 1° C. or less over several minutes, such as over a six-minute period of time.

The pulsed energy may be applied to a plurality of eye tissue areas, wherein adjacent eye tissue areas are separated by at least a predetermined distance to avoid thermal tissue damage. The pulsed energy may be applied to a first eye tissue area and, after a predetermined period of time within a single treatment session, the pulsed energy is reapplied to the first eye tissue area. During an interval between pulsed energy applications to the first eye tissue area, the pulsed energy is applied to a second eye tissue area.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
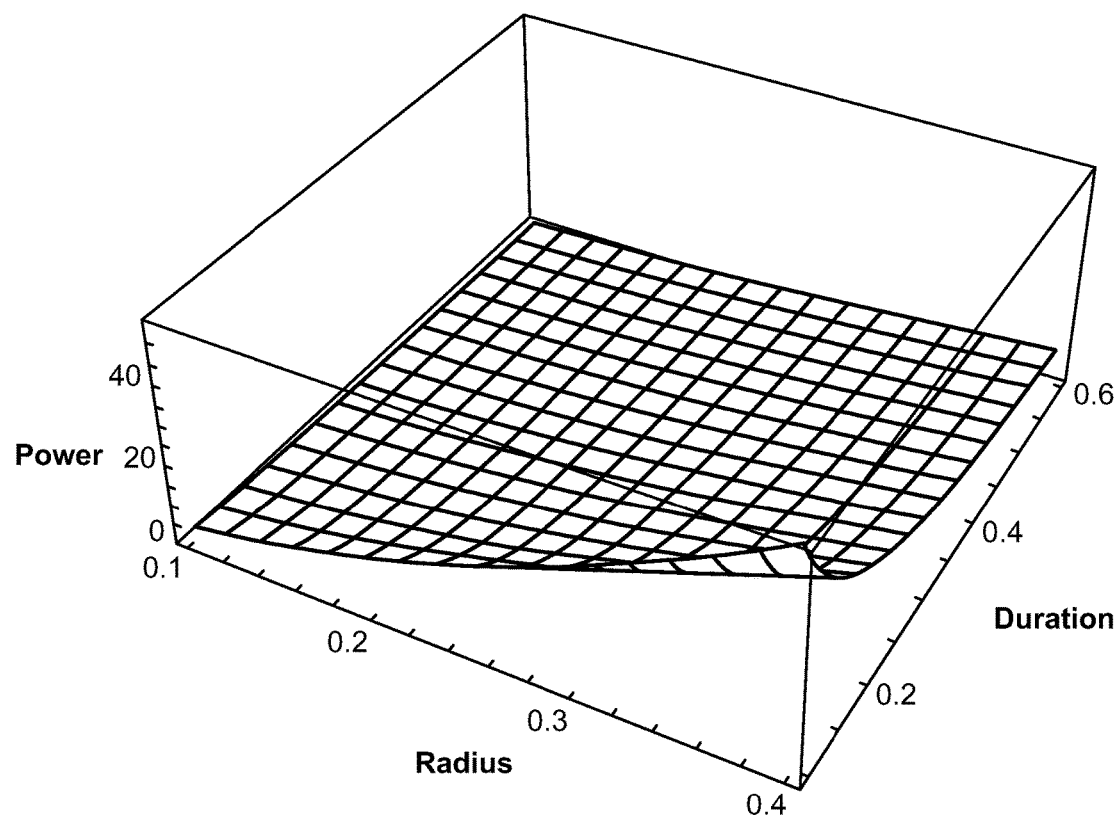
FIG. 1 is a graph illustrating an average power of a laser source having a wavelength compared to a source radius and pulse train duration of the laser.

As shown in the accompanying drawings, and as more fully described herein, the present invention is directed to a process for preventing or treating myopia. This is accomplished by providing a pulsed energy source having energy parameters selected so as to raise an eye tissue temperature sufficiently to achieve a therapeutic or prophylactic effect, while maintaining the average temperature rise of the eye tissue over time at or below a predetermined level so as not to permanently damage the eye tissue.

As indicated above, the prevalence myopia has increased dramatically worldwide within the last few decades. Recent studies have shown that refractive development or myopia is influenced by environmental, behavioral and inherited factors. The inventors believe that there are modifiable biologic factors behind the development of simple, acquired myopia. Low-intensity and high-density subthreshold diode micropulsed laser (SDM) has been demonstrated by the inventors to improve the physiologic and psychophysical function of the eye and optic nerve in a myriad of chronic progressive retinal diseases and open angle glaucoma. Research has indicated that SDM does this by normalizing retinal function and autoregulation by a mechanism referred to by the inventors as "reset to default" effect or homeotrophy. By selectively targeting and normalizing the function of the retinal pigment epithelium (RPE), which is the main driver for retinal function and autoregulation, the biologic function of the RPE, if made abnormal due to environmental or other causes, is reset to default, or returned to normal function. By so doing, the progression of the disease is slowed, stopped or even reversed. The inventors believe that SDM homeotropic therapy, by restoring normal retinal physiology and autoregulation should then slow, stop or even reverse progression of myopia, and particularly pediatric myopia, in the same way that it does other chronic progressive retinopathies and glaucoma. Clinical experience and use in other ocular disorders including diabetic retinopathy, age-related macular degeneration, glaucoma, and inherited retinopathies, suggest that the effective SDM homeotrophic therapy should be both robust and renewable by periodically repeated treatments.

The inventors have discovered that electromagnetic radiation, such as in the form of various wavelengths of laser light, can be applied to retinal tissue in a manner that does not destroy or damage the tissue while achieving beneficial effects on eye diseases. It is believed that this may be due, at least in part, to the stimulation and activation of heat shock proteins and the facilitation of protein repair in the tissue. It is believed that the creation of a thermal time-course stimulates heat shock protein activation or production and facilitates protein repair without causing any damage.

The inventors have found that a laser light beam can be generated that is therapeutic, yet sublethal to retinal tissue cells and thus avoids damaging photocoagulation in the retinal tissue which provides preventative and protective treatment of the retinal tissue of the eye. Various parameters of the light beam must be taken into account and selected so that the combination of the selected parameters achieve the therapeutic effect while not permanently damaging the tissue. These parameters include laser wavelength, radius of the laser source, average laser power, total pulse duration, and duty cycle of the pulse train. Although a laser light beam is used in a particularly preferred embodiment, other pulsed energy sources including ultrasound, ultraviolet frequency, microwave frequency and the like having energy parameters appropriately selected may also be used, but are not as convenient in the treatment of eye disorders and diseases, including myopia, as other diseases and disorders.

The selection of these parameters may be determined by requiring that the Arrhenius integral for HSP activation be greater than 1 or unity. Arrhenius integrals are used for analyzing the impacts of actions on biological tissue. See, for instance, The CRC Handbook of Thermal Engineering, ed. Frank Kreith, Springer Science and Business Media (2000). At the same time, the selected parameters must not permanently damage the tissue. Thus, the Arrhenius integral for damage may also be used, wherein the solved Arrhenius integral is less than 1 or unity.

Alternatively, the FDA/FCC constraints on energy deposition per unit gram of tissue and temperature rise as measured over periods of minutes be satisfied so as to avoid permanent tissue damage. The FDA/FCC requirements on energy deposition and temperature rise are widely used and can be referenced, for example, at www.fda.gov/medicaldevices/deviceregulationandguidance/guidancedocuments/ucm073817.htm#attacha for electromagnetic sources, and Anastosio and P. LaRivero, ed., Emerging Imaging Technologies. CRC Press (2012), for ultrasound sources.

Generally speaking, tissue temperature rises of between 6° C. and 11° C. can create therapeutic effect, such as by activating heat shock proteins, while maintaining the average tissue temperature over a prolonged period of time, such as over several minutes, such as six minutes, below a predetermined temperature, such as 6° C. and even 1° C. or less in certain circumstances, will not permanently damage the tissue.

The subthreshold retinal photocoagulation, sometimes referred to as "true subthreshold", of the invention is defined as retinal laser applications biomicroscopically invisible at the time of treatment. "True subthreshold" photocoagulation, as a result of the present invention, is invisible and includes laser treatment non-discernible by any other known means such as FFA, FAF, or even SD-OCT. "True subthreshold" photocoagulation is therefore defined as a laser treatment which produces absolutely no retinal damage detectable by any means at the time of treatment or any time thereafter by known means of detection. As such, "true subthreshold" is the absence of lesions and other tissue damage and destruction. The invention may be more accurately referred to as photostimulation than photocoagulation due to the absence of typical photocoagulation damage.

Various parameters have been determined to achieve "true subthreshold" or "low-intensity" effective photocoagulation. These include providing sufficient power to produce effective treatment retinal laser exposure, but not too high to create tissue damage or destruction. True subthreshold laser applications can be applied singly or to create a geometric object or pattern of any size and configuration to minimize heat accumulation, but assure uniform heat distribution as well as maximizing heat dissipation such as by using a low duty cycle. The inventor has discovered how to achieve therapeutically effective and harmless true subthreshold retinal laser treatment. The inventor has also discovered that placement of true subthreshold laser applications confluently and contiguously to the retinal surface improves and maximizes the therapeutic benefits of treatment without harm or retinal damage.

It has been found that the intensity or power of a low-duty cycle 810 nm laser beam between 100 watts to 590 watts per square centimeter is effective yet safe. A particularly preferred intensity or power of the laser light beam is approximately 250-350 watts per square centimeter for an 810 nm micropulsed diode laser.

Power limitations in current micropulsed diode lasers require fairly long exposure duration. The longer the laser exposure, the more important the center-spot heat dissipating ability toward the unexposed tissue at the margins of the laser spot and toward the underlying choriocapillaris. Thus, the radiant beam of an 810 nm diode laser should have an exposure envelope duration of 500 milliseconds or less, and preferably approximately 100-300 milliseconds. Of course, if micropulsed diode lasers become more powerful, the exposure duration will be lessened accordingly. It will be understood that the exposure envelope duration is a duration of time where the micropulsed laser beam would be exposed to the same spot or location of the retina, although the actual time of exposure of the tissue to the laser is much less as the laser light pulse is less than a millisecond in duration, and typically between 50 microseconds to 100 microseconds in duration.

Invisible phototherapy or true subthreshold photocoagulation in accordance with the present invention can be performed at various laser light wavelengths, such as from a range of 532 nm to 1300 nm. Use of a different wavelength can impact the preferred intensity or power of the laser light beam and the exposure envelope duration in order that the retinal tissue is not damaged, yet therapeutic effect is achieved.

Another parameter of the present invention is the duty cycle (the frequency of the train of micropulses, or the length of the thermal relaxation time in between consecutive pulses). It has been found that the use of a 10% duty cycle or higher adjusted to deliver micropulsed laser at similar irradiance at similar MPE levels significantly increase the risk of lethal cell injury, particularly in darker fundi. However, duty cycles less than 10%, and preferably approximately 5% duty cycle or less have demonstrated adequate thermal rise and treatment at the level of the RPE cell to stimulate a biologic response, but remained below the level expected to produce lethal cell injury, even in darkly pigmented fundi. Moreover, if the duty cycle is less than 5%, the exposure envelope duration in some instances can exceed 500 milliseconds.

In a particularly preferred embodiment, the use of small retinal laser spots is used. This is due to the fact that larger spots can contribute to uneven heat distribution and insufficient heat dissipation within the large retinal laser spot, potentially causing tissue damage or even tissue destruction towards the center of the larger laser spot. In this usage, "small" would generally apply to retinal spots less than 3 mm in diameter. However, the smaller the retinal spot, the more ideal the heat dissipation and uniform energy application becomes. Thus, at the power intensity and exposure duration described above, small spots, such as 25-300 micrometers in diameter, or small geometric lines or other objects are preferred so as to maximize even heat distribution and heat dissipation to avoid tissue damage.

Thus, the following key parameters have been found in order to create harmless, "true subthreshold", sublethal micropulsed laser light beam to achieve the aims of the present invention, including wavelength or frequency, duty cycle and pulse duration. The laser light beam should have a wavelength greater than 532 nm to avoid cytotoxic photochemical effects, such as a wavelength between 550 nm and 1300 nm, and in a particularly preferred embodiment between 810 nm and 1000 nm. The duty cycle should be less than 10%, and preferably between 2.5%-5%. The pulse train duration or exposure time should be between 100 and 600 milliseconds. The intensity or power of the laser light beam should be between 100-590 watts per square centimeter at the retina or approximately 1 watt per laser spot for each treatment spot at the retina. This is sufficient power to produce retinal laser exposures between 18-55 times Maximum Permissible Exposure (MPE) and retinal irradiance of between 100-590 W/cm$^2$. Preferably, small spot size is used to minimize heat accumulation and assure uniform heat distribution within a given laser spot so as to maximize heat dissipation.

Using the foregoing parameters, a harmless yet therapeutically effective "true subthreshold" or invisible phototherapy treatment can be attained in which retinal photostimulation of all areas of the RPE may be exposed to the laser radiation and preserved and available to contribute therapeutically. The present invention has been found to produce the benefits of conventional photocoagulation and phototherapy while avoiding the drawbacks and complications of conventional phototherapy. In accordance with the present invention, the physician may apply the laser light beam to treat the entire retina, including sensitive areas such as the macula and even the fovea, without creating visual loss or other damage. This is not possible using conventional phototherapies as it could create damage to the eye or even blindness.

It is conventional thinking that tissue damage and lesions must be created in order to have a therapeutic effect. However, the inventors have found that this simply is not the case. In the absence of laser-induced retinal damage, there is no loss of functional retinal tissue and no inflammatory response to treatment. Adverse treatment effects are thus completely eliminated and functional retina preserved rather than sacrificed. This may yield superior visual acuity results compared to conventional photocoagulation treatment.

The present invention spares the neurosensory retina and is selectively absorbed by the RPE. Current theories of the pathogenesis of retinal vascular disease especially implicate cytokines, potent extra cellular vasoactive factors produced by the RPE, as important mediators of retinal vascular disease. The present invention both selectively targets and avoids lethal buildup within RPE. Thus, with the present invention the capacity for the treated RPE to participate in a therapeutic response is preserved and even enhanced rather than eliminated as a result their destruction of the RPE in conventional photocoagulation therapies.

It has been noted that the clinical effects of cytokines may follow a "U-shaped curve" where small physiologic changes in cytokine production, denoted by the left side of curve, may have large clinical effects comparable to high-dose (pharmacologic) therapy (denoted by the right side of the curve). Using sublethal laser exposures in accordance with the present invention may be working on the left side of the curve where the treatment response may approximate more of an "on/off" phenomenon rather than a dose-response. This might explain the clinical effectiveness of the present invention observed at low reported irradiances. This is also consistent with clinical experience and in-vitro studies of laser-tissue interaction, wherein increasing irradiance may simply increase the risk of thermal retinal damage without improving the therapeutic effect.

Another mechanism through which SDM is believed to work is the activation of heat shock proteins (HSPs). Despite a near infinite variety of possible cellular abnormalities, cells of all types share a common and highly conserved mechanism of repair: heat shock proteins (HSPs). HSPs are elicited almost immediately, in seconds to minutes, by almost any type of cell stress or injury. In the absence of lethal cell injury, HSPs are extremely effective at repairing and returning the viable cell toward a more normal functional state. Although HSPs are transient, generally peaking in hours and persisting for a few days, their effects may be long lasting. HSPs reduce inflammation, a common factor in many retinal disorders, including diabetic retinopathy (DR) and AMD.

Laser treatment induces HSP activation and, in the case of retinal treatment, thus alters and normalizes retinal cytokine expression. The more sudden and severe the non-lethal cellular stress (such as laser irradiation), the more rapid and robust HSP production. Thus, a burst of repetitive low temperature thermal spikes at a very steep rate of change (~7° C. elevation with each 100 µs micropulse, or 70,000° C./sec) produced by each SDM exposure is especially effective in stimulating production of HSPs, particularly compared to non-lethal exposure to subthreshold treatment with continuous wave lasers, which can duplicate only the low average tissue temperature rise.

Laser wavelengths below 532 nm produce increasingly cytotoxic photochemical effects. At 532 nm-1300 nm, and particularly 880 nm-1000 nm, SDM produces photothermal, rather than photochemical, cellular stress. Thus, SDM is able to affect the tissue, including RPE, without damaging it. Consistent with HSP activation, SDM produces prompt clinical effects, such as rapid and significant improvement in retinal electrophysiology, visual acuity, contrast visual acuity and improved macular sensitivity measured by microperimetry, as well as long-term effects, such as reduction of DME and involution of retinal neovascularization.

In the retina, the clinical benefits of SDM are thus produced by sub-lethal photothermal RPE HSP activation. In dysfunctional RPE cells, HSP stimulation by SDM results in normalized cytokine expression, and consequently improved retinal structure and function. The therapeutic effects of this "low-intensity" laser/tissue interaction are then amplified by "high-density" laser application, recruiting all the dysfunctional RPE in the targeted area, thereby maximizing the treatment effect. These principles define the treatment strategy of SDM described herein. The ability of SDM to produce therapeutic effects similar to both drugs and photocoagulation indicates that laser-induced retinal damage (for effects other than cautery) is unnecessary and non-therapeutic; and, in fact, detrimental because of the loss of retinal function and incitement of inflammation.

Because normally functioning cells are not in need of repair, HSP stimulation in normal cells would tend to have no notable clinical effect. The "patho-selectivity" of near infrared laser effects, such as SDM, affecting sick cells but not affecting normal ones, on various cell types is consistent with clinical observations of SDM. This facility is key to the suitability of SDM for early and preventative treatment of eyes with chronic progressive disease and eyes with minimal retinal abnormality and minimal dysfunction. Finally, SDM has been reported to have a clinically broad therapeutic range, unique among retinal laser modalities, consistent with American National Standards Institute "Maximum Permissible Exposure" predictions. While SDM may cause direct photothermal effects such as entropic protein unfolding and disaggregation, SDM appears optimized for clinically safe and effective stimulation of HSP-mediated retinal repair.

As SDM does not produce laser-induced retinal damage (photocoagulation), and has no known adverse treatment effect, and has been reported to be an effective treatment in a number of retinal disorders (including diabetic macular edema (DME) proliferative diabetic retinopathy (PDR), macular edema due to branch retinal vein occlusion (BRVO), central serous chorioretinopathy (CSR), reversal of drug tolerance, and prophylactic treatment of progressive degenerative retinopathies such as dry age-related macular degeneration, Stargardts' disease, cone dystrophies, and retinitis pigmentosa. The safety of SDM is such that it may be used transfoveally in eyes with 20/20 visual acuity to reduce the risk of visual loss due to early fovea-involving DME.

As noted above, while SDM stimulation of HSPs is non-specific with regard to the disease process, the result of HSP mediated repair is by its nature specific to the state of the dysfunction. HSPs tend to fix what is wrong, whatever that might be. Thus, the observed effectiveness of SDM in retinal conditions as widely disparate as BRVO, DME, PDR, CSR, age-related and genetic retinopathies, and drug-tolerant NAMD. Conceptually, this facility can be considered a sort of "Reset to Default" mode of SDM action. For the wide range of disorders in which cellular function is critical, SDM normalizes cellular function by triggering a "reset" (to the "factory default settings") via HSP-mediated cellular repair.

The inventors have found that SDM treatment of patients suffering from age-related macular degeneration (AMD) can slow the progress or even stop the progression of AMD. Most of the patients have seen significant improvement in dynamic functional log MAR mesoptic visual acuity and mesoptic contrast visual acuity after the SDM treatment. It is believed that SDM works by targeting, preserving, and "normalizing" (moving toward normal) function of the retinal pigment epithelium (RPE).

SDM has also been shown to stop or reverse the manifestations of the diabetic retinopathy disease state without treatment-associated damage or adverse effects, despite the persistence of systemic diabetes mellitus. On this basis it is hypothesized that SDM might work by inducing a return to more normal cell function and cytokine expression in diabetes-affected RPE cells, analogous to hitting the "reset" button of an electronic device to restore the factory default settings. Based on the above information and studies, SDM treatment may directly affect cytokine expression via heat shock protein (HSP) activation in the targeted tissue.

As indicated above, subthreshold diode micropulsed laser (SDM) photostimulation has been effective in stimulating direct repair of slightly misfolded proteins in eye tissue. Besides HSP activation, another way this may occur is because the spikes in temperature caused by the micropulses in the form of a thermal time-course allows diffusion of water inside proteins, and this allows breakage of the peptide-peptide hydrogen bonds that prevent the protein from returning to its native state. The diffusion of water into proteins results in an increase in the number of restraining hydrogen bonds by a factor on the order of a thousand. Thus, it is believed that this process could be applied to other diseases advantageously as well.

As explained above, the energy source to be applied to the target tissue will have energy and operating parameters which must be determined and selected so as to achieve the therapeutic effect while not permanently damaging the tissue. Using a light beam energy source, such as a laser light beam, as an example, the laser wavelength, duty cycle and total pulse train duration parameters must be taken into account. Other parameters which can be considered include the radius of the laser source as well as the average laser power. Adjusting or selecting one of these parameters can have an effect on at least one other parameter.

Figure 2:
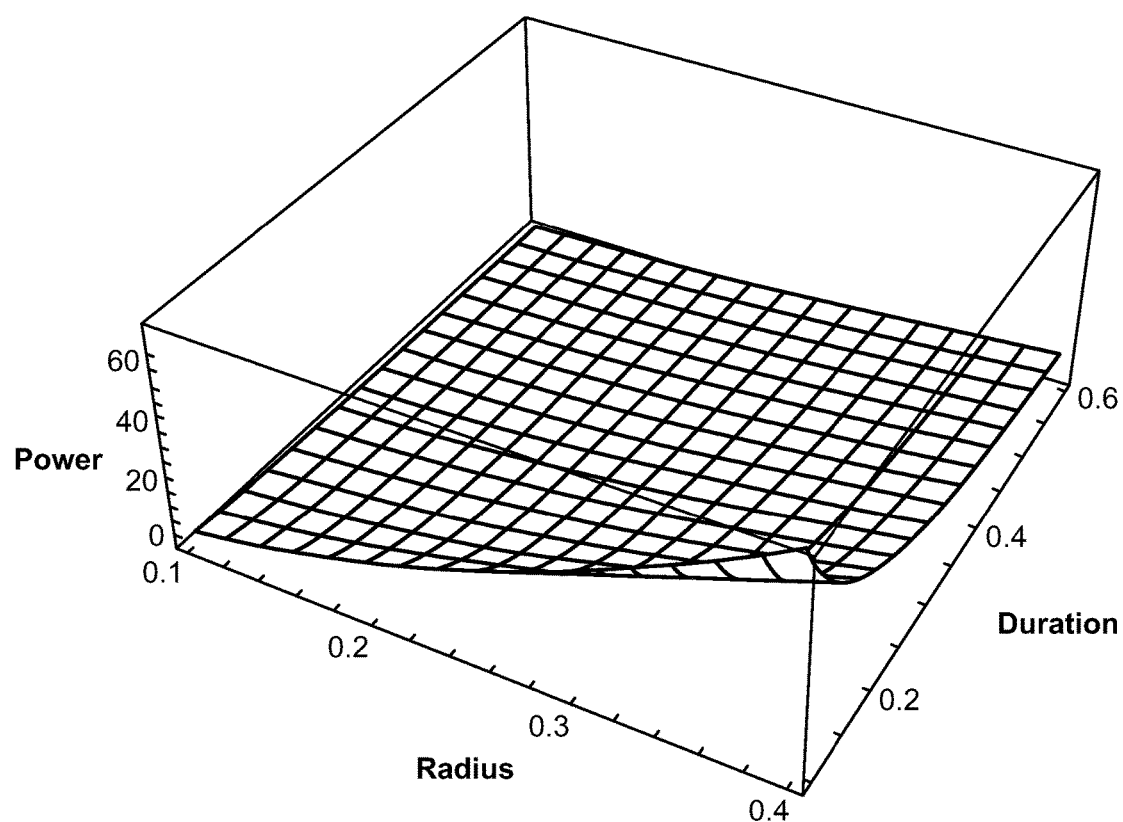
FIG. 2 is a graph similar to FIG. 1, illustrating the average power of a laser source of a higher wavelength compared to a source radius and a pulse train duration of the laser.

FIGS. 1 and 2 illustrate graphs showing the average power in watts as compared to the laser source radius (between 0.1 cm and 0.4 cm) and pulse train duration (between 0.1 and 0.6 seconds). FIG. 1 shows a wavelength of 880 nm, whereas FIG. 2 has a wavelength of 1000 nm. It can be seen in these figures that the required power decreases monotonically as the radius of the source decreases, as the total train duration increases, and as the wavelength decreases. The preferred parameters for the radius of the laser source is 1 mm-4 mm. For a wavelength of 880 nm, the minimum value of power is 0.55 watts, with a radius of the laser source being 1 mm, and the total pulse train duration being 600 milliseconds. The maximum value of power for the 880 nm wavelength is 52.6 watts when the laser source radius is 4 mm and the total pulse drain duration is 100 milliseconds. However, when selecting a laser having a wavelength of 1000 nm, the minimum power value is 0.77 watts with a laser source radius of 1 mm and a total pulse train duration of 600 milliseconds, and a maximum power value of 73.6 watts when the laser source radius is 4 mm and the total pulse duration is 100 milliseconds. The corresponding peak powers, during an individual pulse, are obtained from the average powers by dividing by the duty cycle.

The volume of the tissue region to be heated is determined by the wavelength, the absorption length in the relevant tissue, and by the beam width. The total pulse duration and the average laser power determine the total energy delivered to heat up the tissue, and the duty cycle of the pulse train gives the associated spike, or peak, power associated with the average laser power. Preferably, the pulsed energy source energy parameters are selected so that approximately 20 to 40 joules of energy is absorbed by each cubic centimeter of the target tissue.

It has been determined that the target tissue can be heated to up to approximately 11° C. for a short period of time, such as less than one second, to create the therapeutic effect of the invention while maintaining the target tissue average temperature to a lower temperature range, such as less than 6° C. or even 1° C. or less over a prolonged period of time, such as several minutes. The selection of the duty cycle and the total pulse train duration provide time intervals in which the heat can dissipate. A duty cycle of less than 10%, and preferably between 2.5% and 5%, with a total pulse duration of between 100 milliseconds and 600 milliseconds has been found to be effective.

It has been found that the average temperature rise of the desired target region increasing at least 6° C. and up to 11° C., and preferably approximately 10° C., during the total irradiation period results in HSP activation. The control of the target tissue temperature is determined by choosing source and target parameters such that the Arrhenius integral for HSP activation is larger than 1, while at the same time assuring compliance with the conservative FDA/FCC requirements for avoiding damage or a damage Arrhenius integral being less than 1.

In order to meet the conservative FDA/FCC constraints to avoid permanent tissue damage, for light beams, and other electromagnetic radiation sources, the average temperature rise of the target tissue over any six-minute period is 1° C. or less. The phrase "average temperature rise" as used herein means the target tissue total temperature increase over several minutes, such as up to six minutes, comparing the initial target tissue temperature before application of the pulsed energy source and the target tissue temperature at several minutes, such as six minutes, after the application of the pulsed energy source to the target tissue as a net, or total, temperature increase over the time period. The typical decay times required for the temperature in the heated target region to decrease by thermal diffusion from a temperature rise of approximately 10° C. to 1° C. when the wavelength is 880 nm and the source diameter is 1 millimeter, the temperature decay time is 16 seconds. The temperature decay time is 107 seconds when the source diameter is 4 mm. When the wavelength is 1000 nm, the temperature decay time is 18 seconds when the source diameter is 1 mm and 136 seconds when the source diameter is 4 mm. This is well within the time of the average temperature rise being maintained over the course of several minutes, such as 6 minutes or less. While the target tissue's temperature is raised, such as to approximately 10° C., very quickly, such as in a fraction of a second during the application of the energy source to the tissue, the relatively low duty cycle provides relatively long periods of time between the pulses of energy applied to the tissue and the relatively short pulse train duration ensure sufficient temperature diffusion and decay within a relatively short period of time comprising several minutes, such as 6 minutes or less, that there is no permanent tissue damage.

The pulse train mode of energy delivery has a distinct advantage over a single pulse or gradual mode of energy delivery, as far as the activation of remedial HSPs and the facilitation of protein repair is concerned. There are two considerations that enter into this advantage: first, a big advantage for HSP activation and protein repair in an SDM energy delivery mode comes from producing a spike temperature of the order of 10° C. This large rise in temperature has a big impact on the Arrhenius integrals that describe quantitatively the number of HSPs that are activated and the rate of water diffusion into the proteins that facilitates protein repair. This is because the temperature enters into an exponential that has a big amplification effect. Second, it is important that the temperature rise not remain at the high value (10° C. or more) for long, because then it would violate the FDA and FCC requirements that over periods of minutes the average temperature rise must be less than 1° C. (or in the case of ultrasound 6° C.).

An SDM mode of energy delivery uniquely satisfies both of these foregoing considerations by judicious choice of the power, pulse time, pulse interval, and the volume of the target region to be treated. The volume of the treatment region enters because the temperature must decay from its high value of the order of 10° C. fairly rapidly in order for the long term average temperature rise not to exceed the long term FDA/FCC limit of 6° C. for ultrasound frequencies and 1° C. or less for electromagnetic radiation energy sources.

Figure 3:
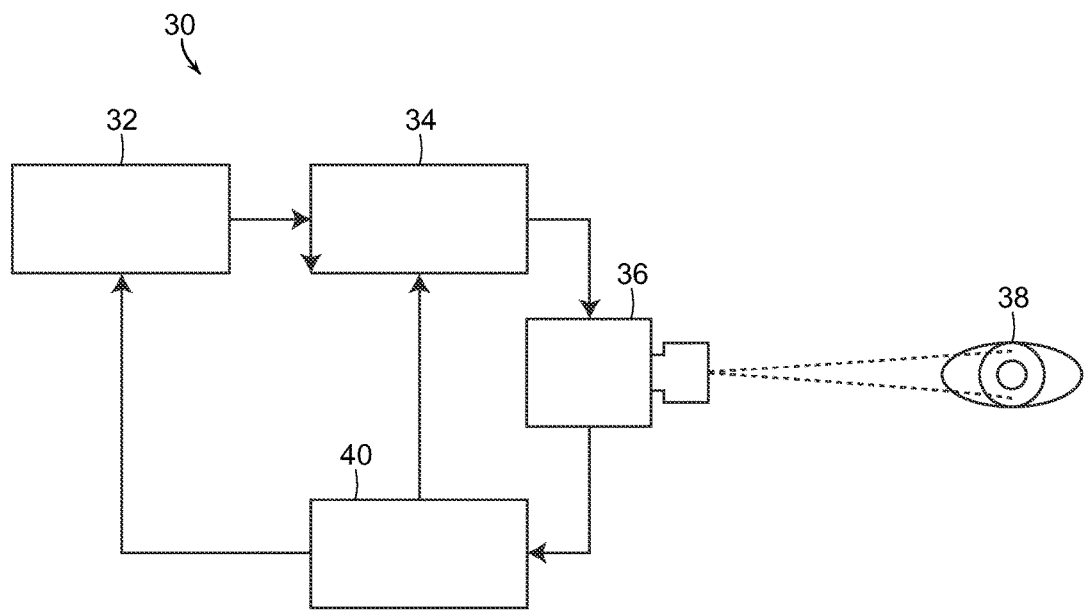
FIG. 3 is a diagrammatic view illustrating a system used for treating an eye in accordance with the present invention.

With reference now to FIG. 3, a schematic diagram is shown of a system for realizing the process of the present invention. The system, generally referred to by the reference number 30, includes a laser console 32, such as for example the 810 nm near infrared micropulsed diode laser in the preferred embodiment. The laser generates a laser light beam which is passed through optics, such as an optical lens or mask, or a plurality of optical lenses and/or masks 34 as needed. The laser projector optics 34 pass the shaped light beam to a coaxial wide-field non-contact digital optical viewing system/camera 36 for projecting the laser beam light onto the eye 38 of the patient. It will be understood that the box labeled 36 can represent both the laser beam projector as well as a viewing system/camera, which might in reality comprise two different components in use. The viewing system/camera 36 provides feedback to a display monitor 40, which may also include the necessary computerized hardware, data input and controls, etc. for manipulating the laser 32, the optics 34, and/or the projection/viewing components 36.

As discussed above, current treatment requires the application of a large number of individual laser beam spots singly applied to the target tissue to be treated. These can number in the hundreds or even thousands for the desired treatment area. This is very time intensive and laborious.

Figure 4:
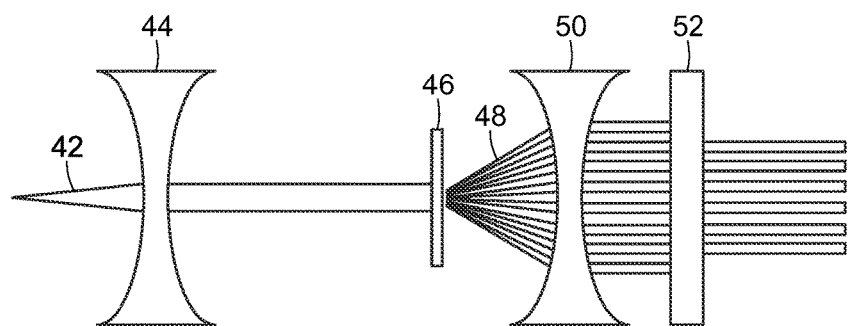
FIG. 4 is a diagrammatic view of an exemplary optical lens or mask used to generate a geometric pattern, in accordance with the present invention.

With reference now to FIG. 4, in one embodiment, the laser light beam 42 is passed through a collimator lens 44 and then through a mask 46. In a particularly preferred embodiment, the mask 46 comprises a diffraction grating. The mask/diffraction grating 46 produces a geometric object, or more typically a geometric pattern of simultaneously produced multiple laser spots or other geometric objects. This is represented by the multiple laser light beams labeled with reference number 48. Alternatively, the multiple laser spots may be generated by a plurality of fiber optic wires. Either method of generating laser spots allows for the creation of a very large number of laser spots simultaneously over a very wide treatment field, such as consisting of the entire retina. In fact, a very high number of laser spots, perhaps numbering in the hundreds, even thousands or more could cover the entire ocular fundus and entire retina, including the macula and fovea, retinal blood vessels and optic nerve. The intent of the process in the present invention is to better ensure complete and total coverage and treatment, sparing none of the retina by the laser so as to improve vision.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements.

The laser light passing through the mask 46 diffracts, producing a periodic pattern a distance away from the mask 46, shown by the laser beams labeled 48 in FIG. 4. The single laser beam 42 has thus been formed into multiple, up to hundreds or even thousands, of individual laser beams 48 so as to create the desired pattern of spots or other geometric objects. These laser beams 48 may be passed through additional lenses, collimators, etc. 50 and 52 in order to convey the laser beams and form the desired pattern on the patient's retina. Such additional lenses, collimators, etc. 50 and 52 can further transform and redirect the laser beams 48 as needed.

Arbitrary patterns can be constructed by controlling the shape, spacing and pattern of the optical mask 46. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Although hundreds or even thousands of simultaneous laser spots could be generated and created and formed into patterns to be applied to the eye tissue, due to the requirements of not overheating the eye tissue, and particularly the eye lens, there are constraints on the number of treatment spots or beams which can be simultaneously used in accordance with the present invention. Each individual laser beam or spot requires a minimum average power over a train duration to be effective. However, at the same time, eye tissue cannot exceed certain temperature rises without becoming damaged. For example, there is a 4° C. restriction on the eye lens temperature rise which would set an upper limit on the average power that can be sent through the lens so as not to overheat and damage the lens of the eye. For example, using an 810 nm wavelength laser, the number of simultaneous spots generated and used could number from as few as 1 and up to approximately 100 when a 0.04 (4%) duty cycle and a total train duration of 0.3 seconds (300 milliseconds) is used for panretinal coverage. The water absorption increases as the wavelength is increased, resulting in heating over the long path length through the vitreous humor in front of the retina. For shorter wavelengths, e.g., 577 nm, the absorption coefficient in the RPE's melanin can be higher, and therefore the laser power can be lower. For example, at 577 nm, the power can be lowered by a factor of 4 for the invention to be effective. Accordingly, there can be as few as a single laser spot or up to approximately 400 laser spots when using the 577 nm wavelength laser light, while still not harming or damaging the eye.

The present invention can use a multitude of simultaneously generated therapeutic light beams or spots, such as numbering in the dozens or even hundreds, as the parameters and methodology of the present invention create therapeutically effective yet non-destructive and non-permanently damaging treatment, allowing the laser light spots to be applied to any portion of the retina, including the fovea, whereas conventional techniques are not able to use a large number of simultaneous laser spots, and are often restricted to only one treatment laser beam, in order to avoid accidental exposure of sensitive areas of the retina, such as the fovea, as these will be damaged from the exposure to conventional laser beam methodologies, which could cause loss of eyesight and other complications.

Figure 5:
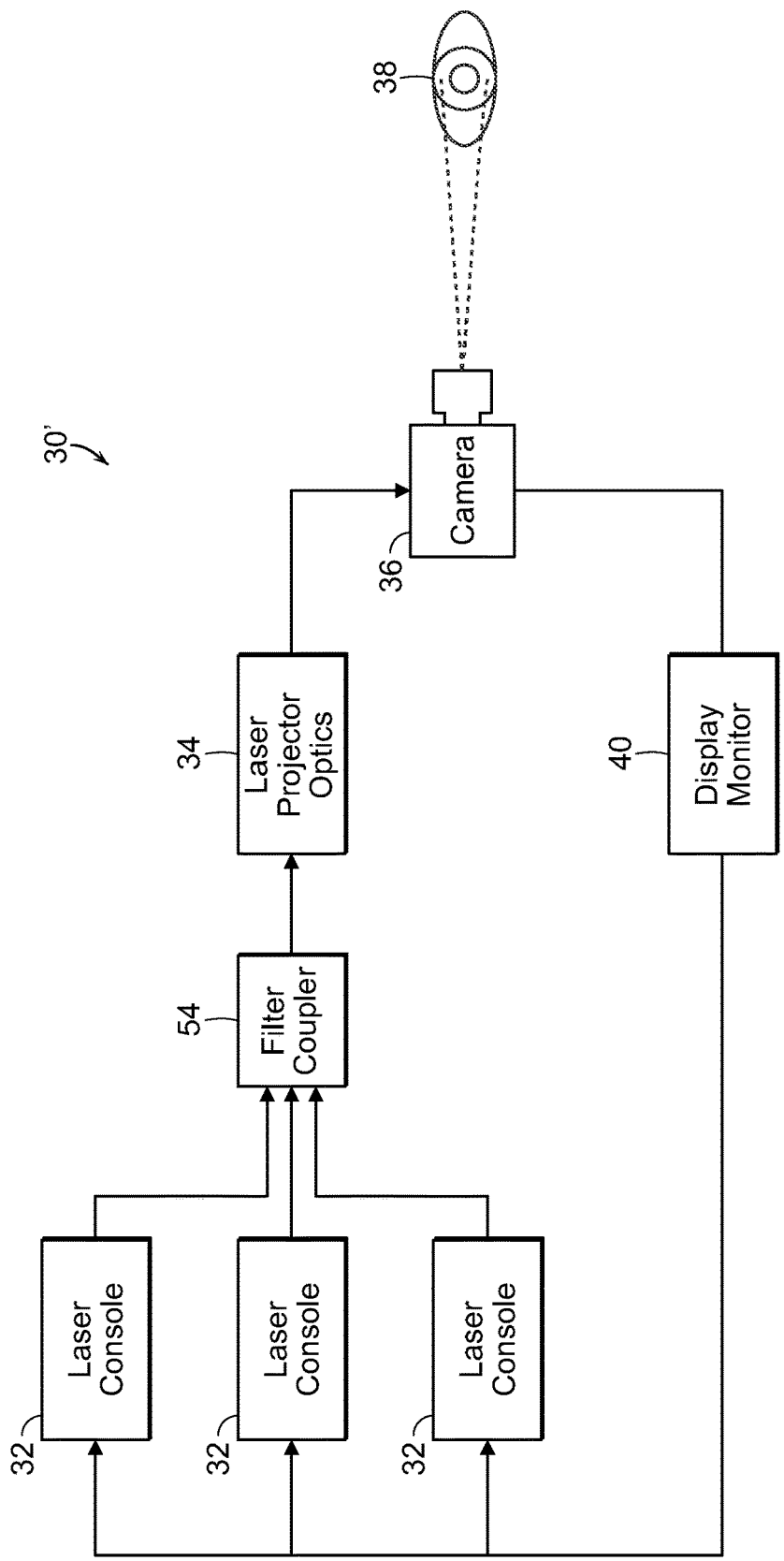
FIG. 5 is a diagrammatic view illustrating an alternate embodiment of a system used for treating eye tissue in accordance with the present invention.

FIG. 5 illustrates diagrammatically a system which couples multiple light sources into the pattern-generating optical subassembly described above. Specifically, this system 30' is similar to the system 30 described in FIG. 3 above. The primary differences between the alternate system 30' and the earlier described system 30 is the inclusion of a plurality of laser consoles 32, the outputs of which are each fed into a fiber coupler 54. The fiber coupler produces a single output that is passed into the laser projector optics 34 as described in the earlier system. The coupling of the plurality of laser consoles 32 into a single optical fiber is achieved with a fiber coupler 54 as is known in the art. Other known mechanisms for combining multiple light sources are available and may be used to replace the fiber coupler described herein.

In this system 30' the multiple light sources 32 follow a similar path as described in the earlier system 30, i.e., collimated, diffracted, recollimated, and directed into the retina with a steering mechanism. In this alternate system 30' the diffractive element must function differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the steering mechanism 36 to the retina 38 for treatment. The slight difference in the diffraction angles will affect how the steering pattern achieves coverage of the retina.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the retina, the application of the other wavelengths achieves either incomplete or overlapping coverage of the retina. The second mode sequentially applies each light source of a varying or different wavelength with the proper steering pattern to achieve complete coverage of the retina for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 6:
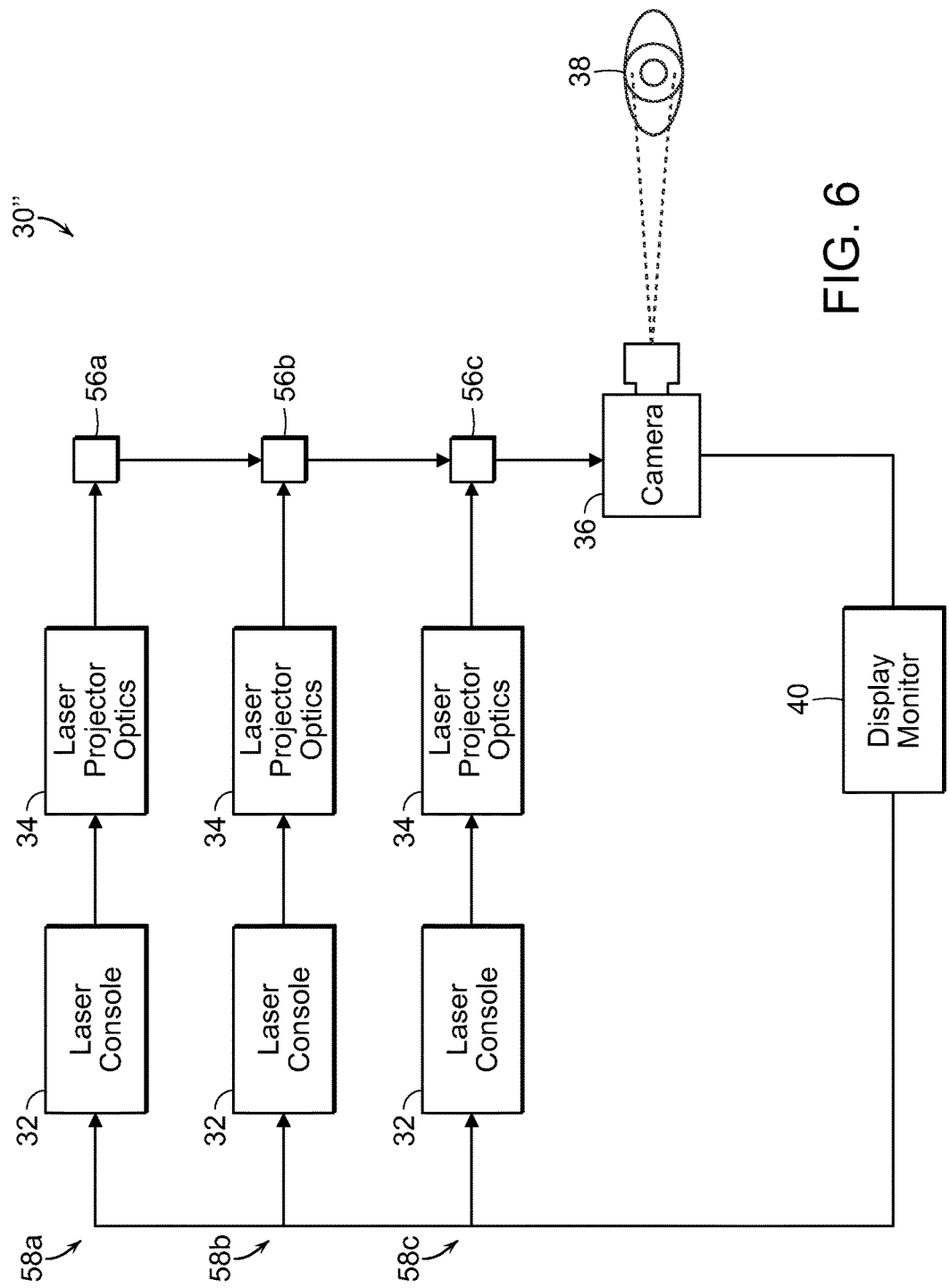
FIG. 6 is a diagrammatic view illustrating yet another alternate embodiment of a system used for treating eye tissue in accordance with the present invention.

FIG. 6 illustrates diagrammatically yet another alternate embodiment of the inventive system 30". This system 30" is configured generally the same as the system 30 depicted in FIG. 3. The main difference resides in the inclusion of multiple pattern-generating subassembly channels tuned to a specific wavelength of the light source. Multiple laser consoles 32 are arranged in parallel with each one leading directly into its own laser projector optics 34. The laser projector optics of each channel 58a, 58b, 58c comprise a collimator 44, mask or diffraction grating 48 and recollimators 50, 52 as described in connection with FIG. 4 above—the entire set of optics tuned for the specific wavelength generated by the corresponding laser console 32. The output from each set of optics 34 is then directed to a beam splitter 56 for combination with the other wavelengths. It is known by those skilled in the art that a beam splitter used in reverse can be used to combine multiple beams of light into a single output.

The combined channel output from the final beam splitter 56c is then directed through the camera 36 which applies a steering mechanism to allow for complete coverage of the retina 38.

In this system 30" the optical elements for each channel are tuned to produce the exact specified pattern for that channel's wavelength. Consequently, when all channels are combined and properly aligned a single steering pattern may be used to achieve complete coverage of the retina for all wavelengths.

The system 30" may use as many channels 58a, 58b, 58c, etc. and beam splitters 56a, 56b, 56c, etc. as there are wavelengths of light being used in the treatment.

Implementation of the system 30" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 30", each channel begins with a light source 32, which could be from an optical fiber as in other embodiments of the pattern-generating subassembly. This light source 32 is directed to the optical assembly 34 for collimation, diffraction, recollimation and directed into the beam splitter which combines the channel with the main output.

The field of photobiology reveals that different biologic effects may be achieved by exposing target tissues to lasers of different wavelengths. The same may also be achieved by consecutively applying multiple lasers of either different or the same wavelength in sequence with variable time periods of separation and/or with different irradiant energies. The present invention anticipates the use of multiple laser, light or radiant wavelengths (or modes) applied simultaneously or in sequence to maximize or customize the desired treatment effects. This method also minimizes potential detrimental effects. The optical methods and systems illustrated and described above provide simultaneous or sequential application of multiple wavelengths.

Figure 7:
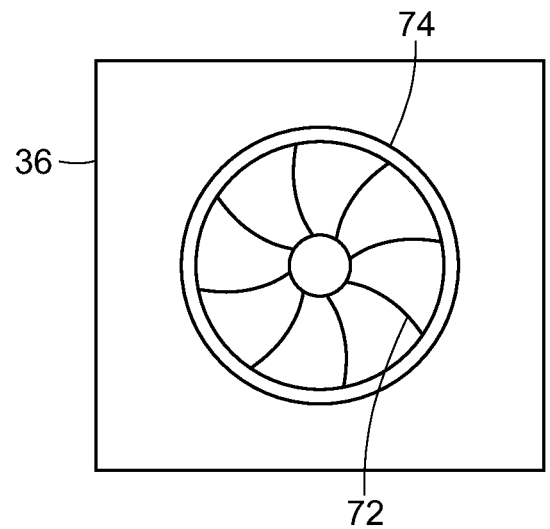
FIG. 7 is a front view of a camera including an iris aperture of the present invention.
Figure 8:
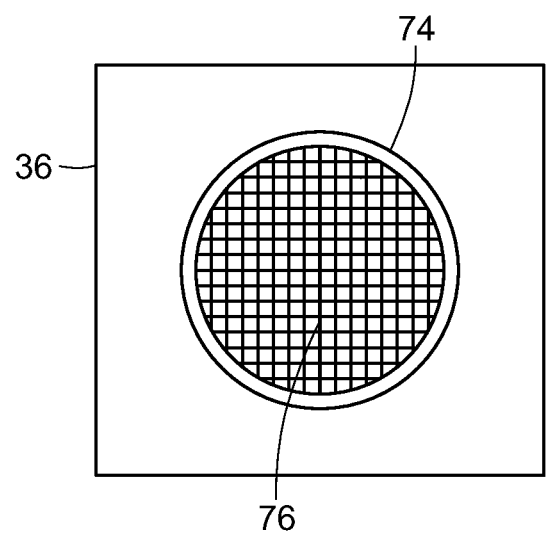
FIG. 8 is a front view of a camera including an LCD aperture, in accordance with the present invention.

The invention described herein is generally safe for panretinal and/or trans-foveal treatment. However, it is possible that a user, i.e., surgeon, preparing to limit treatment to a particular area of the retina where disease markers are located or to prevent treatment in a particular area with darker pigmentation, such as from scar tissue. In this case, the camera 36 may be fitted with an iris aperture 72 configured to selectively widen or narrow the opening through which the light is directed into the eye 38 of the patient. FIG. 7 illustrates an opening 74 on a camera 36 fitted with such an iris aperture 72. Alternatively, the iris aperture 72 may be replaced or supplemented by a liquid crystal display (LCD) 76. The LCD 76 acts as a dynamic aperture by allowing each pixel in the display to either transmit or block the light passing through it. Such an LCD 76 is depicted in FIG. 8.

Preferably, any one of the inventive systems 30, 30', 30" includes a display on a user interface with a live image of the retina as seen through the camera 36. The user interface may include an overlay of this live image of the retina to select areas where the treatment light will be limited or excluded by the iris aperture 72 and/or the LCD 76. The user may draw an outline on the live image as on a touch screen and then select for either the inside or the outside of that outline to have limited or excluded coverage.

By way of example, if the user identifies scar tissue on the retina that should be excluded from treatment, the user would draw an outline around the scar tissue and then mark the interior of that outline for exclusion from the laser treatment. The control system and user interface would then send the proper control signal to the LCD 76 to block the projected treatment light through the pixels over the selected scar tissue. The LCD 76 provides an added benefit of being useful for attenuating regions of the projected pattern. This feature may be used to limit the peak power output of certain spots within the pattern. Limiting the peak power of certain spots in the pattern with the highest power output can be used to make the treatment power more uniform across the retina.

Alternatively, the surgeon may use the fundus monitor to outline an area of the retina to be treated or avoided; and the designated area then treated or avoided by software directing the treatment beams to treat or avoid said areas without need or use of an obstructing LCD 76 diaphragm.

Typically, the system of the present invention incorporates a guidance system to ensure complete and total retinal treatment with retinal photostimulation. This guidance system is to be distinguished from traditional retinal laser guidance systems that are employed to both direct treatment to a specific retinal location; and to direct treatment away from sensitive locations such as the fovea that would be damaged by conventional laser treatment, as the treatment method of the present invention is harmless, the entire retina, including the fovea and even optical nerve, can be treated. Moreover, protection against accidental visual loss by accidental patient movement is not a concern. Instead, patient movement would mainly affect the guidance in tracking of the application of the laser light to ensure adequate coverage. Fixation/tracking/registration systems consisting of a fixation target, tracking mechanism, and linked to system operation are common in many ophthalmic diagnostic systems and can be incorporated into the present invention.

In a particularly preferred embodiment, the geometric pattern of simultaneous laser spots is sequentially offset so as to achieve confluent and complete treatment of the retinal surface. Although a segment of the retina can be treated in accordance with the present invention, more ideally the entire retina will be treated within one treatment session. This is done in a time-saving manner by placing a plurality of spots over the entire ocular fundus at once. This pattern of simultaneous spots is scanned, shifted, or redirected as an entire array sequentially, so as to cover the entire retina in a single treatment session.

Figure 9:
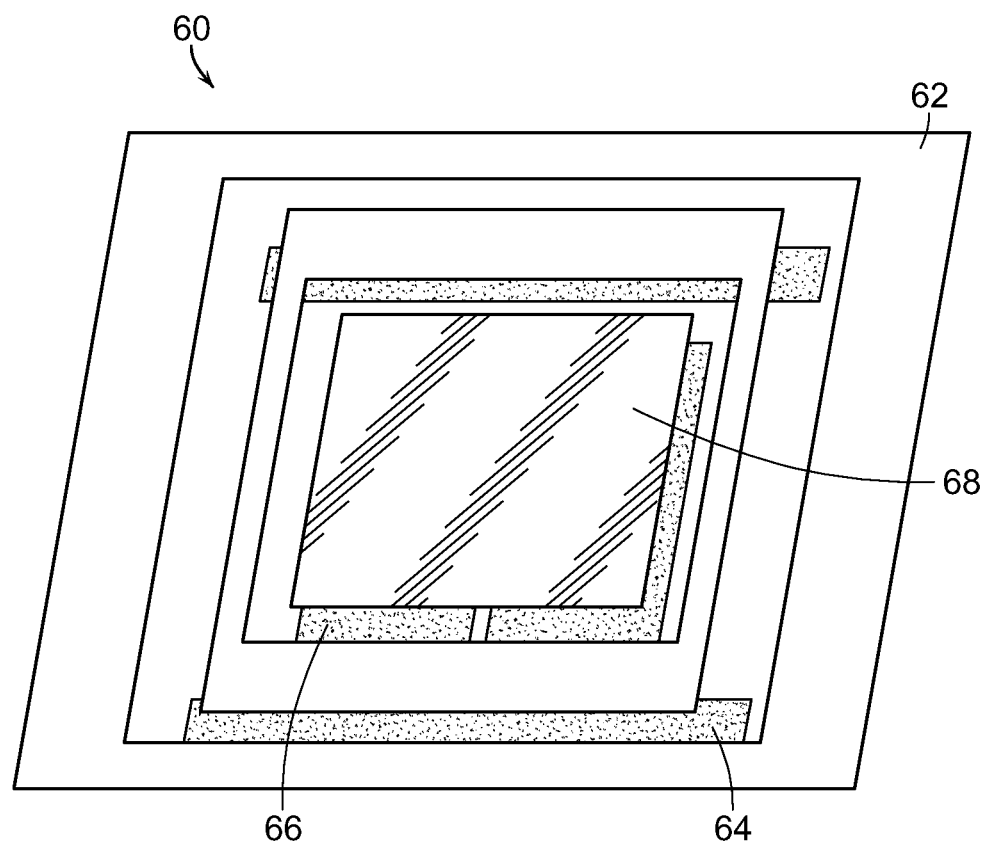
FIG. 9 is a top view of an optical scanning mechanism, used in accordance with the present invention.
Figure 10:
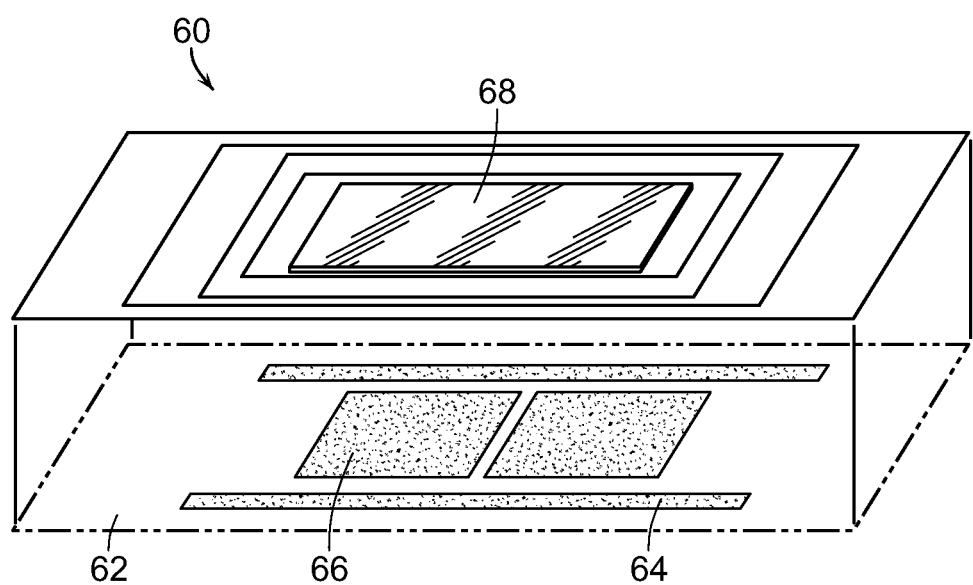
FIG. 10 is a partially exploded view of the optical scanning mechanism of FIG. 9, illustrating various component parts thereof.

This can be done in a controlled manner using an optical scanning mechanism 60. FIGS. 9 and 10 illustrate an optical scanning mechanism 60 which may be used in the form of a MEMS mirror, having a base 62 with electronically actuated controllers 64 and 66 which serve to tilt and pan the mirror 68 as electricity is applied and removed thereto. Applying electricity to the controller 64 and 66 causes the mirror 68 to move, and thus the simultaneous pattern of laser spots or other geometric objects reflected thereon to move accordingly on the retina of the patient. This can be done, for example, in an automated fashion using an electronic software program to adjust the optical scanning mechanism 60 until complete coverage of the retina, or at least the portion of the retina desired to be treated, is exposed to the phototherapy. The optical scanning mechanism may also be a small beam diameter scanning galvo mirror system, or similar system, such as that distributed by Thorlabs. Such a system is capable of scanning the lasers in the desired offsetting pattern.

Figure 11:
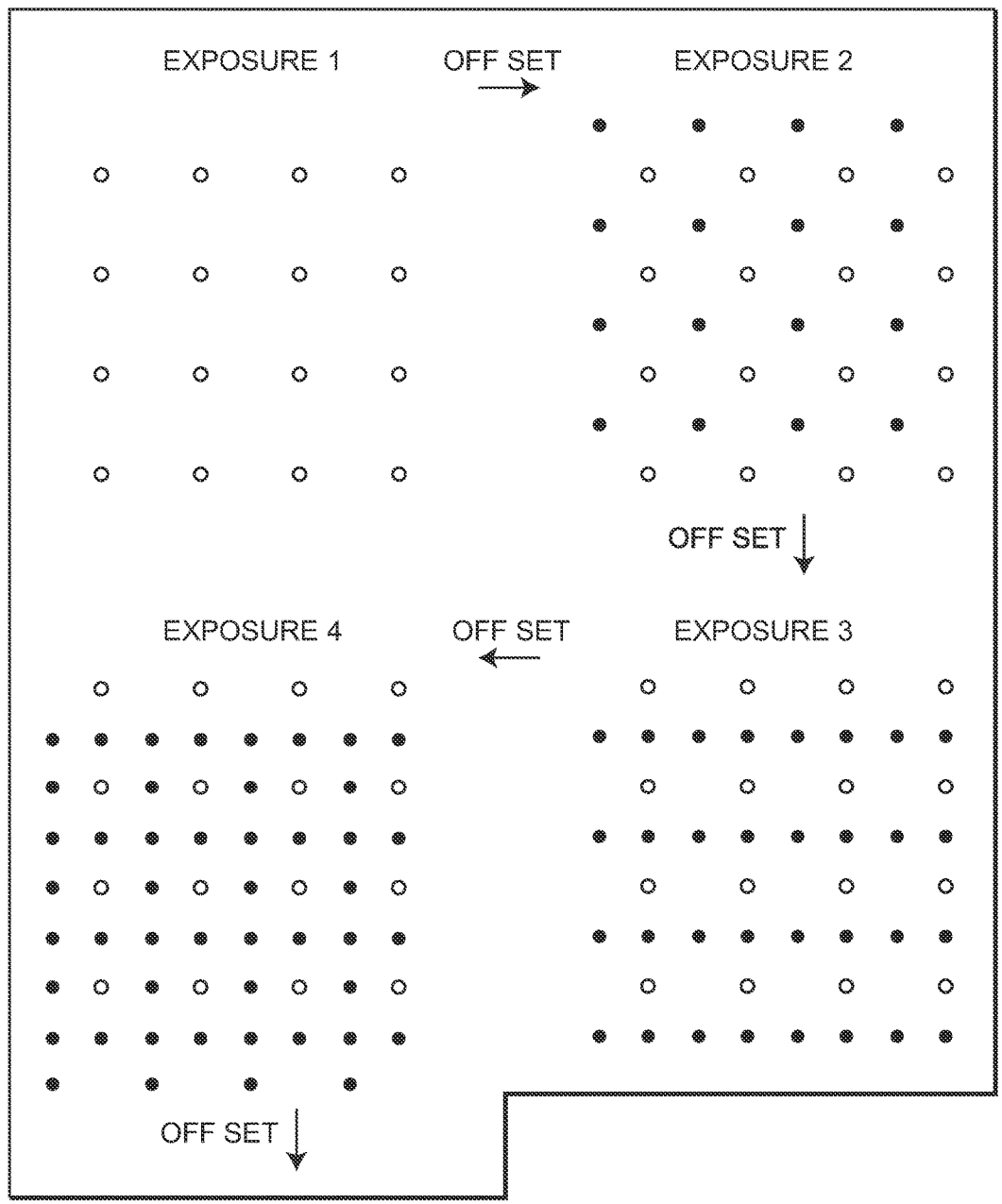
FIG. 11 is a diagrammatic view illustrating controlled offset of exposure of an exemplary geometric pattern grid of laser spots to treat the eye tissue, in accordance with the present invention.

Since the parameters of the present invention dictate that the applied radiant energy or laser light is not destructive or damaging, the geometric pattern of laser spots, for example, can be overlapped without destroying the tissue or creating any permanent damage. However, in a particularly preferred embodiment, as illustrated in FIG. 11, the pattern of spots are offset at each exposure so as to create space between the immediately previous exposure to allow heat dissipation and prevent the possibility of heat damage or tissue destruction. Thus, as illustrated in FIG. 11, the pattern, illustrated for exemplary purposes as a grid of sixteen spots, is offset each exposure such that the laser spots occupy a different space than previous exposures. It will be understood that the diagrammatic use of circles or empty dots as well as filled dots are for diagrammatic purposes only to illustrate previous and subsequent exposures of the pattern of spots to the area, in accordance with the present invention. The spacing of the laser spots prevents overheating and damage to the tissue. It will be understood that this occurs until the entire retina, the preferred methodology, has received phototherapy, or until the desired effect is attained. This can be done, for example, by a scanning mechanism, such as by applying electrostatic torque to a micromachined mirror, as illustrated in FIGS. 9 and 10. By combining the use of small retina laser spots separated by exposure free areas, prevents heat accumulation, and grids with a large number of spots per side, it is possible to atraumatically and invisibly treat large target areas with short exposure durations far more rapidly than is possible with current technologies.

By rapidly and sequentially repeating redirection or offsetting of the entire simultaneously applied grid array of spots or geometric objects, complete coverage of the target, such as a human retina, can be achieved rapidly without thermal tissue injury. This offsetting can be determined algorithmically to ensure the fastest treatment time and least risk of damage due to thermal tissue, depending on laser parameters and desired application. The following has been modeled using the Fraunhoffer Approximation. With a mask having a nine by nine square lattice, with an aperture radius 9 μm, an aperture spacing of 600 μm, using a 890 nm wavelength laser, with a mask-lens separation of 75 mm, and secondary mask size of 2.5 mm by 2.5 mm, the following parameters will yield a grid having nineteen spots per side separated by 133 μm with a spot size radius of 6 μm. The number of exposures "m" required to treat (cover confluently with small spot applications) given desired area sidelength "A", given output pattern spots per square side "n", separation between spots "R", spot radius "r" and desired square side length to treat area "A", can be given by the following formula:

$$m = \frac{A}{nR} \text{ floor}\left(\frac{R}{2r}\right)^2$$

With the foregoing setup, one can calculate the number of operations m needed to treat different field areas of exposure. For example, a 3 mm×3 mm area, which is useful for treatments, would require 98 offsetting operations, requiring a treatment time of approximately thirty seconds. Another example would be a 3 cm×3 cm area, representing the entire human retinal surface. For such a large treatment area, a much larger secondary mask size of 25 mm by 25 mm could be used, yielding a treatment grid of 190 spots per side separated by 133 μm with a spot size radius of 6 μm. Since the secondary mask size was increased by the same factor as the desired treatment area, the number of offsetting operations of approximately 98, and thus treatment time of approximately thirty seconds, is constant. These treatment times represent at least ten to thirty times reduction in treatment times compared to current methods of sequential individual laser spot applications. Field sizes of 3 mm would, for example, allow treatment of the entire human macula in a single exposure, useful for treatment of common blinding conditions such as diabetic macular edema and age-related macular degeneration. Performing the entire 98 sequential offsettings would ensure entire coverage of the macula.

Of course, the number and size of retinal spots produced in a simultaneous pattern array can be easily and highly varied such that the number of sequential offsetting operations required to complete treatment can be easily adjusted depending on the therapeutic requirements of the given application.

Furthermore, by virtue of the small apertures employed in the diffraction grating or mask, quantum mechanical behavior may be observed which allows for arbitrary distribution of the laser input energy. This would allow for the generation of any arbitrary geometric shapes or patterns, such as a plurality of spots in grid pattern, lines, or any other desired pattern. Other methods of generating geometric shapes or patterns, such as using multiple fiber optical fibers or microlenses, could also be used in the present invention. Time savings from the use of simultaneous projection of geometric shapes or patterns permits the treatment fields of novel size, such as the 1.2 cm^2 area to accomplish whole-retinal treatment, in a single clinical setting or treatment session.

Figure 12:
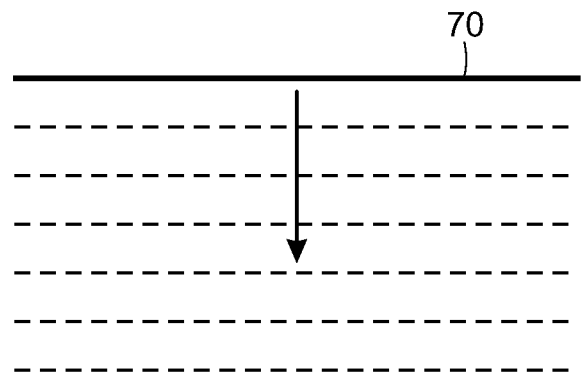
FIG. 12 is a diagrammatic view illustrating units of a geometric object in the form of a line controllably scanned to treat an area of eye tissue, in accordance with the present invention.
Figure 13:
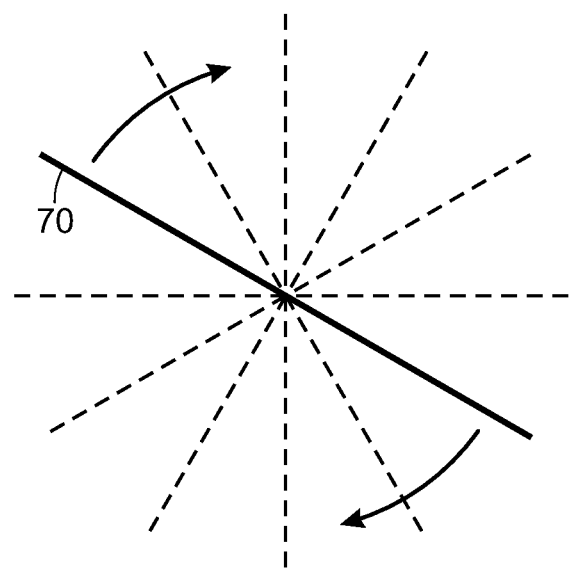
FIG. 13 is a diagrammatic view similar to FIG. 12, but illustrating the geometric line or bar rotated to treat an area of the retina, in accordance with the present invention.

With reference now to FIGS. 12 and 13, instead of a geometric pattern of small laser spots, the present invention contemplates use of other geometric objects or patterns. For example, a single line 70 of laser light, formed by the continuously or by means of a series of closely spaced spots, can be created. An offsetting optical scanning mechanism can be used to sequentially scan the line over an area, illustrated by the downward arrow in FIG. 12. With reference now to FIG. 13, the same geometric object of a line 70 can be rotated, as illustrated by the arrows, so as to create a circular field of phototherapy. The potential negative of this approach, however, is that the central area will be repeatedly exposed, and could reach unacceptable temperatures. This could be overcome, however, by increasing the time between exposures, or creating a gap in the line such that the central area is not exposed.

Power limitations in current pulsed diode lasers require fairly long exposure duration. The longer the exposure, the more important the center-spot heat dissipating ability toward the unexposed tissue at the margins of the laser spot and toward the underlying choriocapillaris as in the retina. Thus, the pulsed laser light beam of an 810 nm diode laser should have an exposure envelope duration of 500 milliseconds or less, and preferably approximately 300 milliseconds. Of course, if micropulsed diode lasers become more powerful, the exposure duration should be lessened accordingly.

Aside from power limitations, another parameter of the present invention is the duty cycle, or the frequency of the train of micropulses, or the length of the thermal relaxation time between consecutive pulses. It has been found that the use of a 10% duty cycle or higher adjusted to deliver micropulsed laser at similar irradiance at similar MPE levels significantly increase the risk of lethal cell injury, particularly in darker fundi. However, duty cycles of less than 10%, and preferably 5% or less demonstrate adequate thermal rise and treatment at the level of the MPE cell to stimulate a biological response, but remain below the level expected to produce lethal cell injury, even in darkly pigmented fundi. The lower the duty cycle, however, the exposure envelope duration increases, and in some instances can exceed 500 milliseconds.

Each micropulsed lasts a fraction of a millisecond, typically between 50 microseconds to 100 microseconds in duration. Thus, for the exposure envelope duration of 300-500 milliseconds, and at a duty cycle of less than 5%, there is a significant amount of wasted time between micropulses to allow the thermal relaxation time between consecutive pulses. Typically, a delay of between 1 and 3 milliseconds, and preferably approximately 2 milliseconds, of thermal relaxation time is needed between consecutive pulses. For adequate treatment, the retinal cells are typically exposed or hit by the laser light between 50-200 times, and preferably between 75-150 at each location. With the 1-3 milliseconds of relaxation or interval time, the total time in accordance with the embodiments described above to treat a given area, or more particularly the locations on the retina which are being exposed to the laser spots is between 200 milliseconds and 500 milliseconds on average. The thermal relaxation time is required so as not to overheat the cells within that location or spot and so as to prevent the cells from being damaged or destroyed. While time periods of 200-500 milliseconds do not seem long, given the small size of the laser spots and the need to treat a relatively large area of the retina, treating the entire macula or the entire retina can take a significant amount of time, particularly from the perspective of a patient who is undergoing treatment.

Accordingly, the present invention may utilize the interval between consecutive laser light applications to the same location (typically between 1 to 3 milliseconds) to apply the laser light to a second treatment area, or additional areas, of the retina and/or fovea that is spaced apart from the first treatment area. The laser beams are returned to the first treatment location, or previous treatment locations, within the predetermined interval of time so as to provide sufficient thermal relaxation time between consecutive pulses, yet also sufficiently treat the cells in those locations or areas properly by sufficiently increasing the temperature of those cells over time by repeatedly applying the laser light to that location in order to achieve the desired therapeutic benefits of the invention.

It is important to return to a previously treated location within 1-3 milliseconds, and preferably approximately 2 milliseconds, to allow the area to cool down sufficiently during that time, but also to treat it within the necessary window of time. For example, one cannot wait one or two seconds and then return to a previously treated area that has not yet received the full treatment necessary, as the treatment will not be as effective or perhaps not effective at all. However, during that interval of time, typically approximately 2 milliseconds, at least one other area, and typically multiple areas, can be treated with a laser light application as the laser light pulses are typically 50 microseconds to 100 microseconds in duration. The number of additional areas which can be treated is limited only by the micopulse duration and the ability to controllably move the laser light beams from one area to another. Currently, approximately four additional areas which are sufficiently spaced apart from one another can be treated during the thermal relaxation intervals beginning with a first treatment area. Thus, multiple areas can be treated, at least partially, during the 200-500 millisecond exposure envelope for the first area. Thus, in a single interval of time, instead of only 100 simultaneous light spots being applied to a treatment area, approximately 500 light spots can be applied during that interval of time in different treatment areas. This would be the case, for example, for a laser light beam having a wavelength of 810 nm. For shorter wavelengths, such as 570 nm, even a greater number of individual locations can be exposed to the laser beams to create light spots. Thus, instead of a maximum of approximately 400 simultaneous spots, approximately 2,000 spots could be covered during the interval between micropulsed treatments to a given area or location.

As mentioned above, typically each location has between 50-200, and more typically between 75-150, light applications applied thereto over the course of the exposure envelope duration (typically 200-500 milliseconds) to achieve the desired treatment. In accordance with an embodiment of the present invention, the laser light would be reapplied to previously treated areas in sequence during the relaxation time intervals for each area or location. This would occur repeatedly until a predetermined number of laser light applications to each area to be treated have been achieved.

Figure 14A:
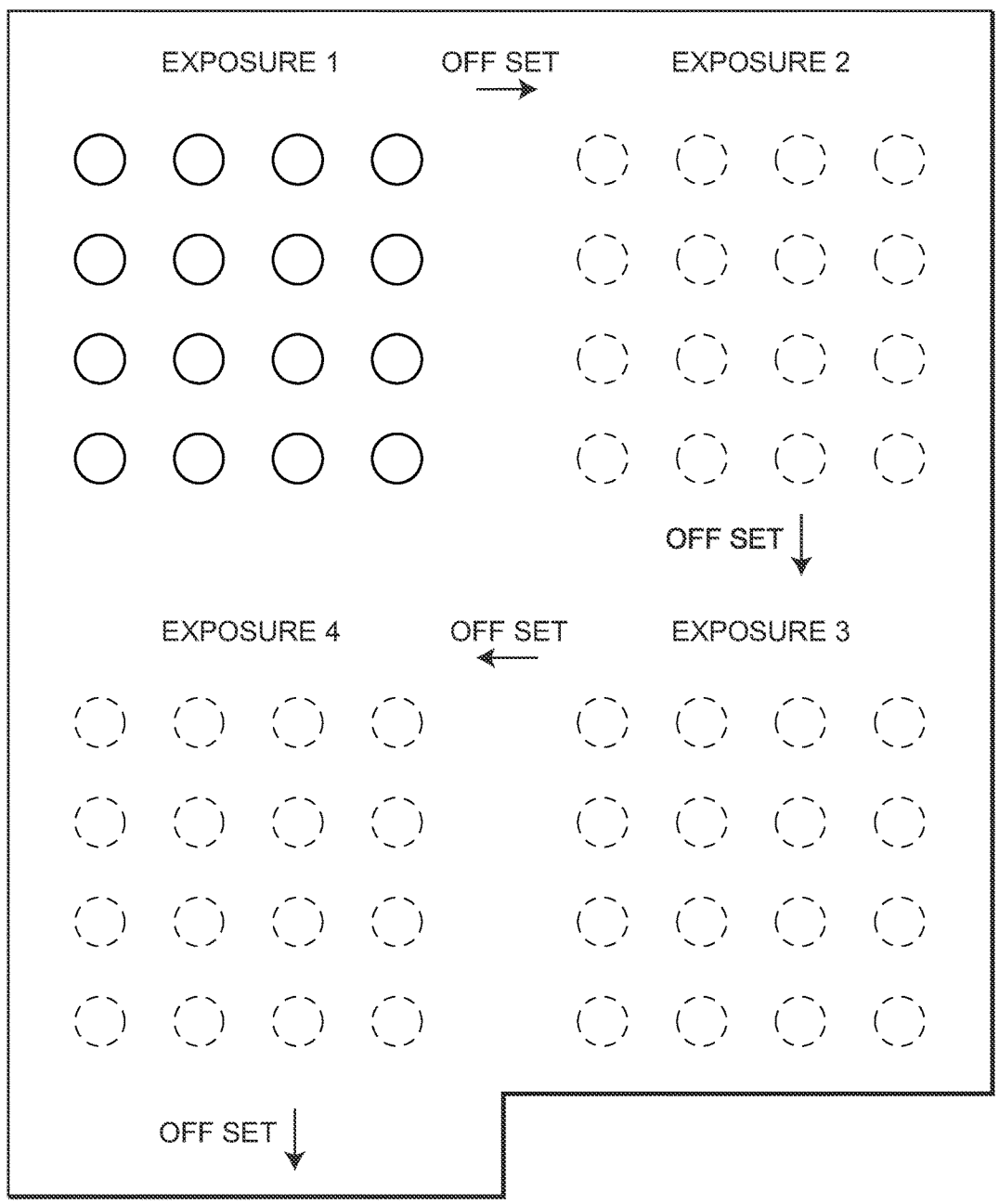
FIG. 14A-FIG. 14D are diagrammatic views illustrating the application of laser light to different treatment areas during a predetermined interval of time, within a single treatment session, and reapplying the laser light to previously treated areas, in accordance with the present invention.
Figure 14B:
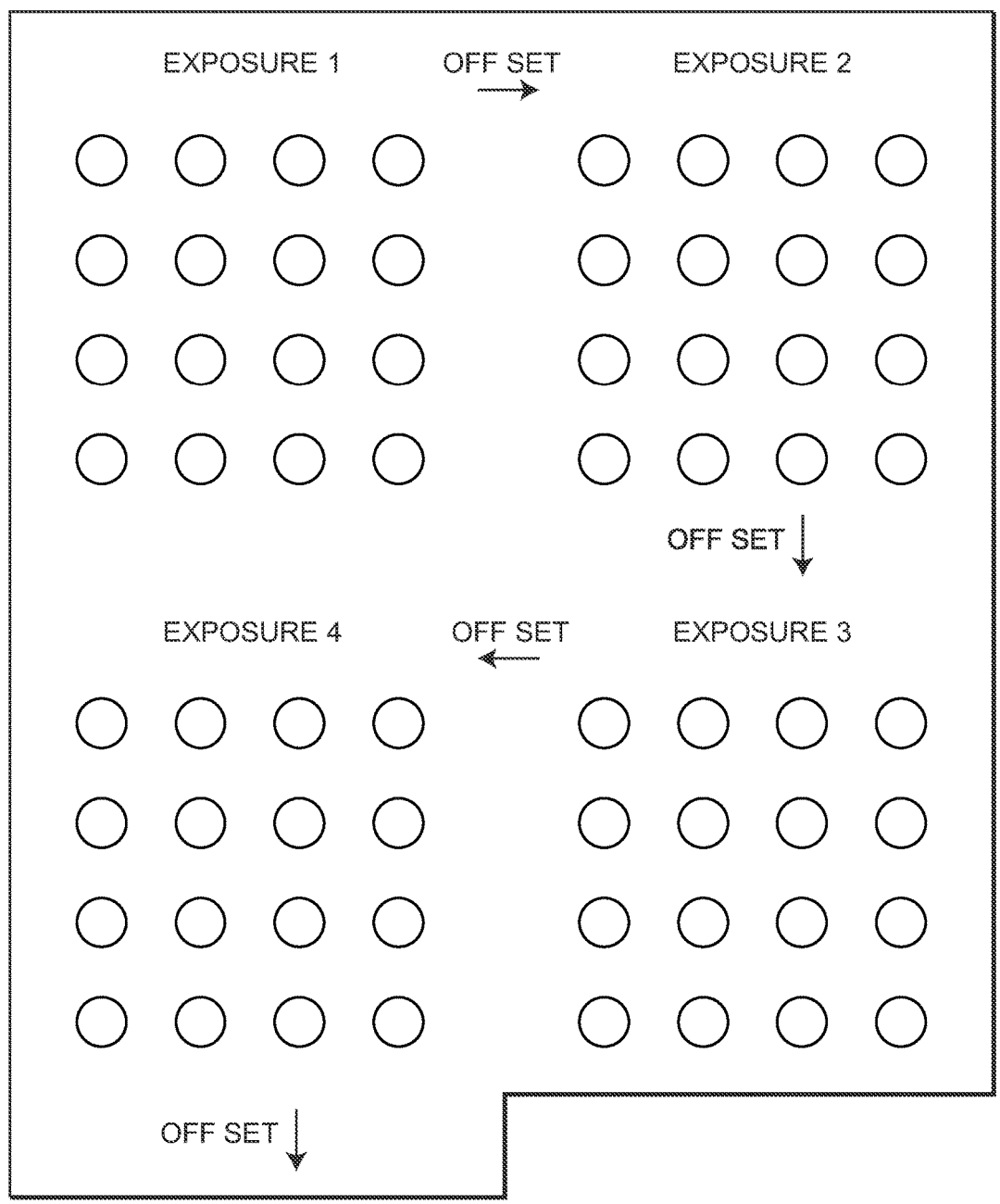
Figure 14C:
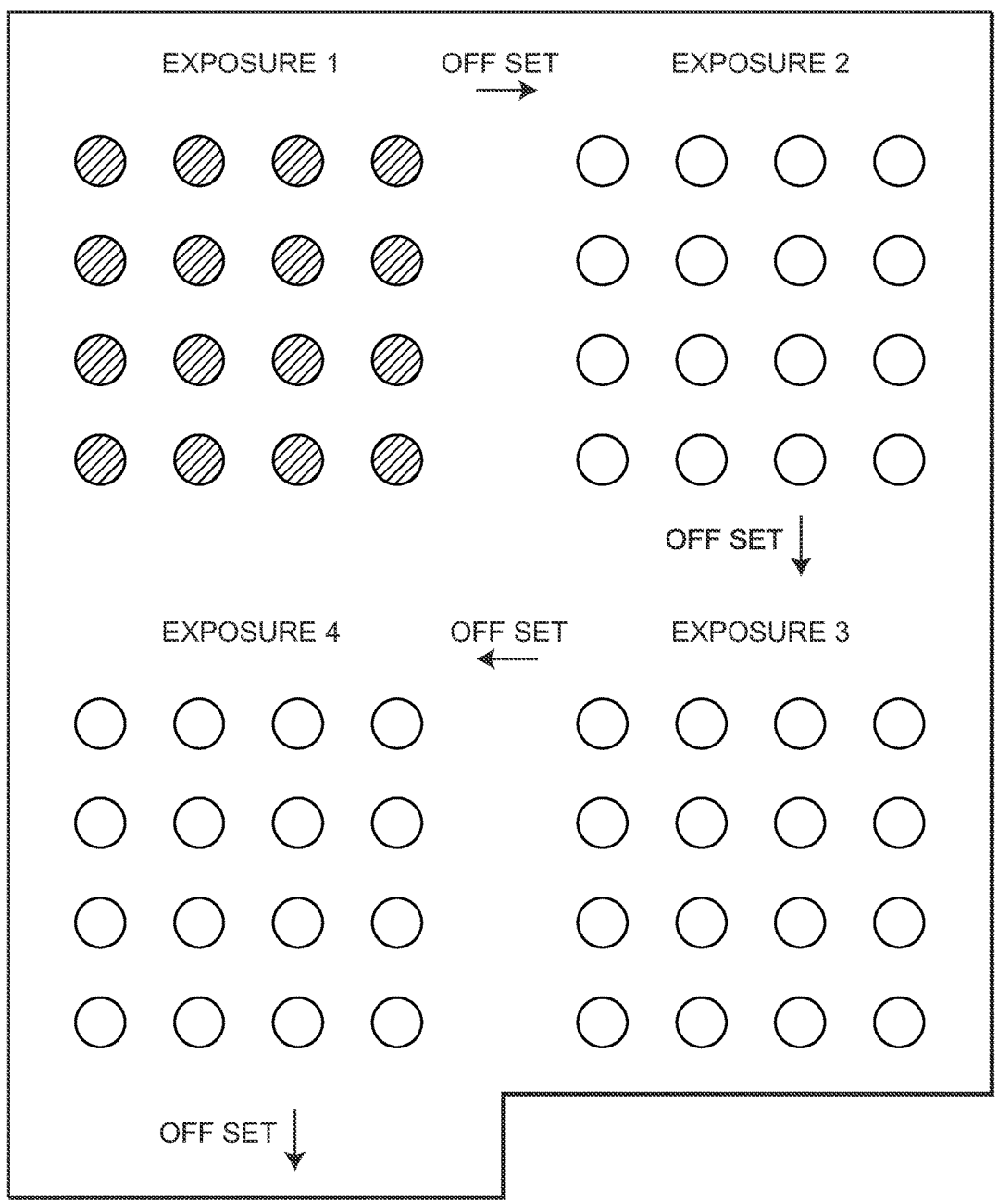
Figure 14D:
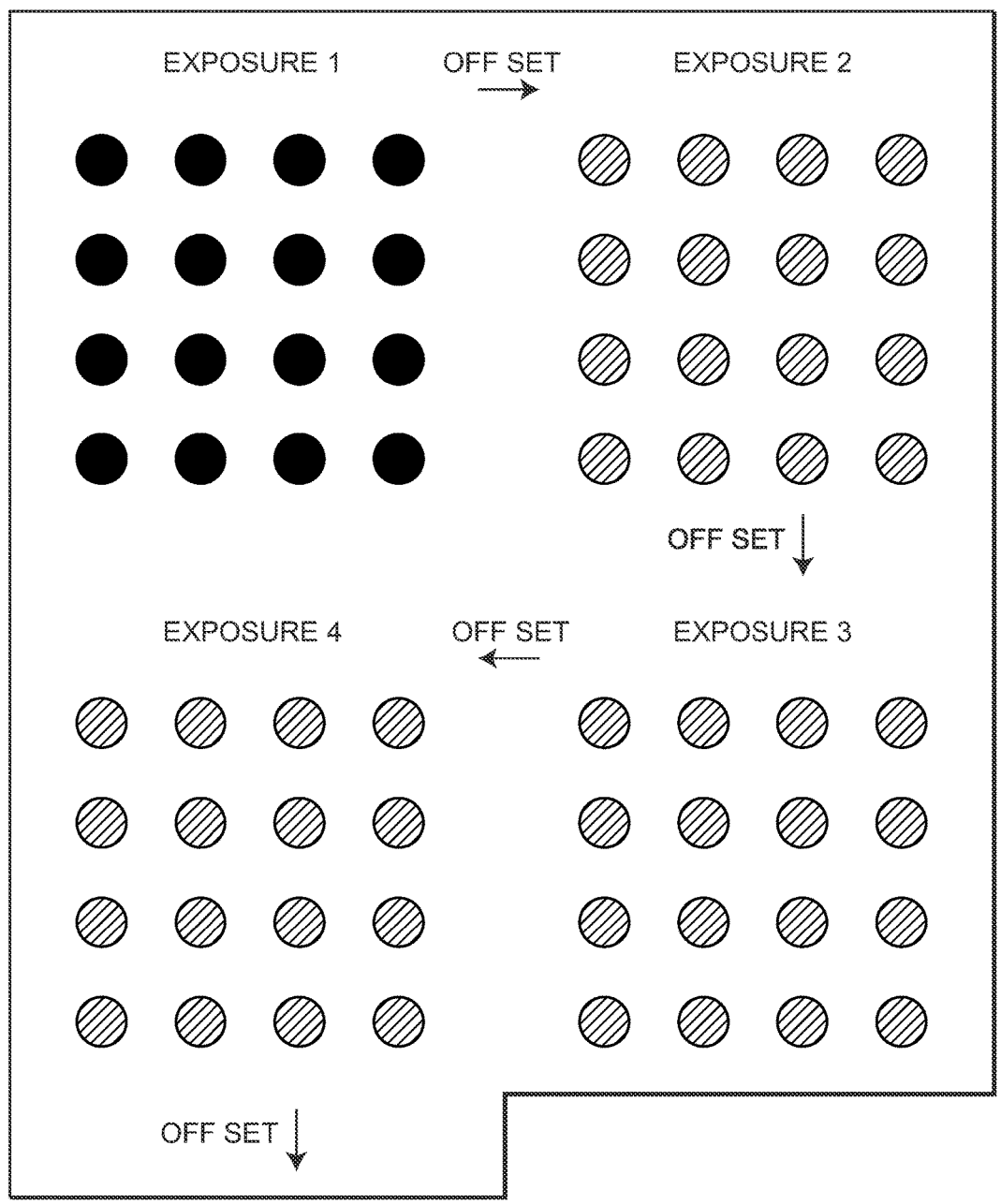

This is diagrammatically illustrated in FIGS. 14A-14D. FIG. 14A illustrates with solid circles a first area having laser light applied thereto as a first application. The laser beams are offset or microshifted to a second exposure area, followed by a third exposure area and a fourth exposure area, as illustrated in FIG. 14B, until the locations in the first exposure area need to be retreated by having laser light applied thereto again within the thermal relaxation time interval. The locations within the first exposure area would then have laser light reapplied thereto, as illustrated in FIG. 14C. Secondary or subsequent exposures would occur in each exposure area, as illustrated in FIG. 14D by the increasingly shaded dots or circles until the desired number of exposures or hits or light applications had been achieved to therapeutically treat these areas, diagrammatically illustrated by the blackened circles in exposure area 1 in FIG. 14D. When a first or previous exposure area has been completed treated, this enables the system to add an additional exposure area, which process is repeated until the entire area of retina to be treated has been fully treated. It should be understood that the use of solid circles, broken line circles, partially shaded circles, and fully shaded circles are for explanatory purposes only, as in fact the exposure of the laser light in accordance with the present invention is invisible and non-detectable to both the human eye as well as known detection devices and techniques.

Adjacent exposure areas must be separated by at least a predetermined minimum distance to avoid thermal tissue damage. Such distance is at least 0.5 diameter away from the immediately preceding treated location or area, and more preferably between 1-2 diameters away. Such spacing relates to the actually treated locations in a previous exposure area. It is contemplated by the present invention that a relatively large area may actually include multiple exposure areas therein which are offset in a different manner than that illustrated in FIG. 14. For example, the exposure areas could comprise the thin lines illustrated in FIGS. 12 and 13, which would be repeatedly exposed in sequence until all of the necessary areas were fully exposed and treated. In accordance with the present invention, this can comprise a limited area of the retina, the entire macula or panmacular treatment, or the entire retina, including the fovea. However, due to the methodology of the present invention, the time required to treat that area of the retina to be treated or the entire retina is significantly reduced, such as by a factor of 4 or 5 times, such that a single treatment session takes much less time for the medical provider and the patient need not be in discomfort for as long of a period of time.

Figure 15:
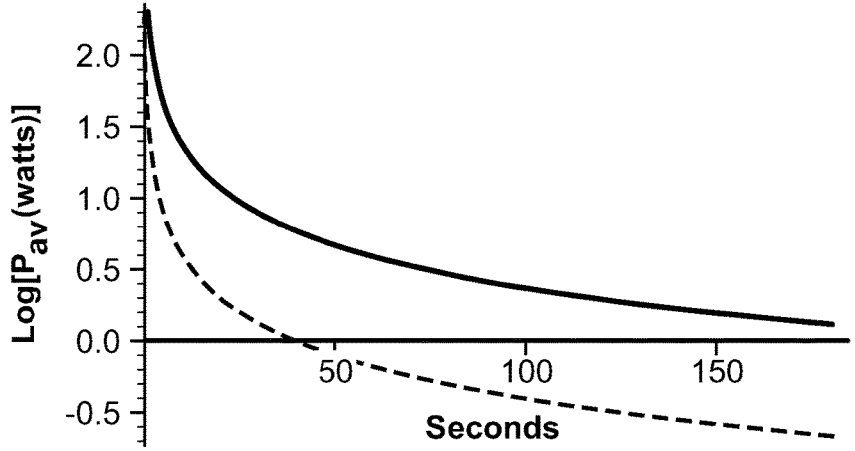
FIGS. 15-17 are graphs depicting the relationship of treatment power and time in accordance with embodiments of the present invention.
Figure 16:
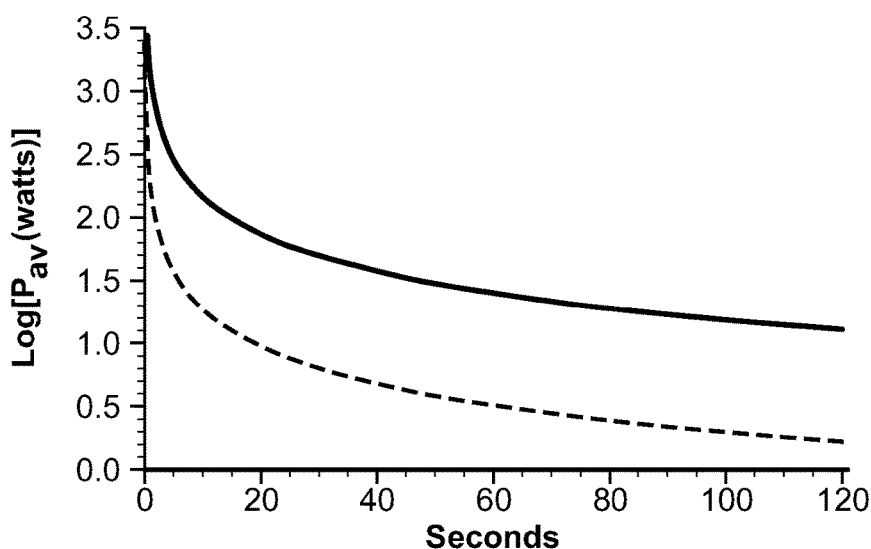
Figure 17:
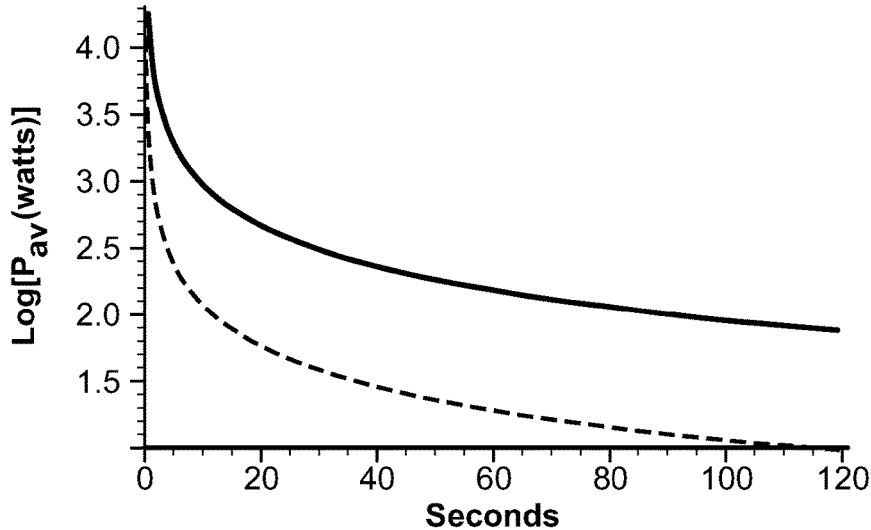

In accordance with this embodiment of the invention of applying one or more treatment beams to the retina at once, and moving the treatment beams to a series of new locations, then bringing the beams back to retreat the same location or area repeatedly has been found to also require less power compared to the methodology of keeping the laser beams in the same locations or area during the entire exposure envelope duration. With reference to FIGS. 15-17, there is a linear relationship between the pulse length and the power necessary, but there is a logarithmic relationship between the heat generated.

With reference to FIG. 15, a graph is provided wherein the x-axis represents the Log of the average power in watts and the y-axis represents the treatment time, in seconds. The lower curve is for panmacular treatment and the upper curve is for panretinal treatment. This would be for a laser light beam having a micropulse time of 50 microseconds, a period of 2 milliseconds period of time between pulses, and duration of train on a spot of 300 milliseconds. The areas of each retinal spot are 100 microns, and the laser power for these 100 micron retinal spots is 0.74 watts. The panmacular area is 0.55 cm$^2$, requiring 7,000 panmacular spots total, and the panretinal area is 3.30 cm$^2$, requiring 42,000 laser spots for full coverage. Each RPE spot requires a minimum energy in order for its reset mechanism to be adequately activated, in accordance with the present invention, namely, 38.85 joules for panmacular and 233.1 joules for panretinal. As would be expected, the shorter the treatment time, the larger the required average power. However, there is an upper limit on the allowable average power, which limits how short the treatment time can be.

As mentioned above, there are not only power constraints with respect to the laser light available and used, but also the amount of power that can be applied to the eye without damaging eye tissue. For example, temperature rise in the lens of the eye is limited, such as between 4° C. so as not to overheat and damage the lens, such as causing cataracts. Thus, an average power of 7.52 watts could elevate the lens temperature to approximately 4° C. This limitation in power increases the minimum treatment time.

However, with reference to FIG. 16, the total power per pulse required is less in the microshift case of repeatedly and sequentially moving the laser spots and returning to prior treated locations, so that the total energy delivered and the total average power during the treatment time is the same. FIGS. 16 and 17 show how the total power depends on treatment time. This is displayed in FIG. 16 for panmacular treatment, and in FIG. 17 for panretinal treatment. The upper, solid line or curve represents the embodiment where there are no microshifts taking advantage of the thermal relaxation time interval, such as described and illustrated in FIG. 11, whereas the lower dashed line represents the situation for such microshifts, as described and illustrated in FIG. 14. FIGS. 16 and 17 show that for a given treatment time, the peak total power is less with microshifts than without microshifts. This means that less power is required for a given treatment time using the microshifting embodiment of the present invention. Alternatively, the allowable peak power can be advantageously used, reducing the overall treatment time.

Thus, in accordance with FIGS. 15-17, a log power of 1.0 (10 watts) would require a total treatment time of 20 seconds using the microshifting embodiment of the present invention, as described herein. It would take more than 2 minutes of time without the microshifts, and instead leaving the micropulsed light beams in the same location or area during the entire treatment envelope duration. There is a minimum treatment time according to the wattage. However, this treatment time with microshifting is much less than without microshifting. As the laser power required is much less with the microshifting, it is possible to increase the power in some instances in order to reduce the treatment time for a given desired retinal treatment area. The product of the treatment time and the average power is fixed for a given treatment area in order to achieve the therapeutic treatment in accordance with the present invention. This could be implemented, for example, by applying a higher number of therapeutic laser light beams or spots simultaneously at a reduced power. Of course, since the parameters of the laser light are selected to be therapeutically effective yet not destructive or permanently damaging to the cells, no guidance or tracking beams are required, only the treatment beams as all areas of the retina, including the fovea, can be treated in accordance with the present invention. In fact, in a particularly preferred embodiment, the entire retina, including the fovea, is treated in accordance with the present invention, which is simply not possible using conventional techniques.

Due to the unique characteristics of the present invention, allowing a single set of optimized laser parameters, which are not significantly influenced by media opacity, retinal thickening, or fundus pigmentation, a simplified user interface is permitted. While the operating controls could be presented and function in many different ways, the system permits a very simplified user interface that might employ only two control functions. That is, an "activate" button, wherein a single depression of this button while in "standby" would actuate and initiate treatment. A depression of this button during treatment would allow for premature halting of the treatment, and a return to "standby" mode. The activity of the machine could be identified and displayed, such as by an LED adjacent to or within the button. A second controlled function could be a "field size" knob. A single depression of this button could program the unit to produce, for example, a 3 mm focal or a "macular" field spot. A second depression of this knob could program the unit to produce a 6 mm or "posterior pole" spot. A third depression of this knob could program the unit to produce a "pan retinal" or approximately 160°-220° panoramic retinal spot or coverage area. Manual turning of this knob could produce various spot field sizes therebetween. Within each field size, the density and intensity of treatment would be identical. Variation of the field size would be produced by optical or mechanical masking or apertures, such as the iris or LCD apertures described below.

Fixation software could monitor the displayed image of the ocular fundus. Prior to initiating treatment of a fundus landmark, such as the optic nerve, or any part or feature of either eye of the patient (assuming orthophoria), could be marked by the operator on the display screen. Treatment could be initiated and the software would monitor the fundus image or any other image-registered to any part of either eye of the patient (assuming orthophoria) to ensure adequate fixation. A break in fixation would automatically interrupt treatment. A break in fixation could be detected optically; or by interruption of low energy infrared beams projected parallel to and at the outer margins of the treatment beam by the edge of the pupil. Treatment would automatically resume toward completion as soon as fixation was established. At the conclusion of treatment, determined by completion of confluent delivery of the desired laser energy to the target, the unit would automatically terminate exposure and default to the "on" or "standby" mode. Due to unique properties of this treatment, fixation interruption would not cause harm or risk patient injury, but only prolong the treatment session.

The laser could be projected via a wide field non-contact lens to the ocular fundus. Customized direction of the laser fields or particular target or area of the ocular fundus other than the central area could be accomplished by an operator joy stick or eccentric patient gaze. The laser delivery optics could be coupled coaxially to a wide field non-contact digital ocular fundus viewing system. The image of the ocular fundus produced could be displayed on a video monitor visible to the laser operator. Maintenance of a clear and focused image of the ocular fundus could be facilitated by a joy stick on the camera assembly manually directed by the operator. Alternatively, addition of a target registration and tracking system to the camera software would result in a completely automated treatment system.

A fixation image could be coaxially displayed to the patient to facilitate ocular alignment. This image would change in shape and size, color, intensity, blink or oscillation rate or other regular or continuous modification during treatment to avoid photoreceptor exhaustion, patient fatigue and facilitate good fixation.

In addition, the results or images from other retinal diagnostic modalities, such as OCT, retinal angiography, or autofluoresence photography, might be displayed in parallel or by superimposition on the display image of the patient's fundus to guide, aid or otherwise facilitate the treatment. This parallel or superimposition of images can facilitate identification of disease, injury or scar tissue on the retina.

The inventors have found that treatment in accordance with the invention of patients suffering from age-related macular degeneration (AMD) can slow the progress or even stop the progression of AMD. Further evidence of this restorative treatment effect is the inventor's finding that treatment can uniquely reduce the risk of vision loss in AMD due to choroidal neovascularization by 80%. Most of the patients have seen significant improvement in dynamic functional log MAR visual acuity and contrast visual acuity after the treatment in accordance with the invention, with some experiencing better vision. It is believed that this works by targeting, preserving, and "normalizing" (moving toward normal) function of the retinal pigment epithelium (RPE).

Treatment in accordance with the invention has also been shown to stop or reverse the manifestations of the diabetic retinopathy disease state without treatment-associated damage or adverse effects, despite the persistence of systemic diabetes mellitus. Studies published by the inventor have shown that the restorative effect of treatment can uniquely reduce the risk of progression of diabetic retinopathy by 85%. On this basis it is hypothesized that the invention might work by inducing a return to more normal cell function and cytokine expression in diabetes-affected RPE cells, analogous to hitting the "reset" button of an electronic device to restore the factory default settings.

Based on the above information and studies, SDM treatment may directly affect cytokine expression and heat shock protein (HSP) activation in the targeted tissue, particularly the retinal pigment epithelium (RPE) layer. Panretinal and panmacular SDM has been noted by the inventors to reduce the rate of progression of many retinal diseases, including severe non-proliferative and proliferative diabetic retinopathy, AMD, DME, etc. The known therapeutic treatment benefits of individuals having these retinal diseases, coupled with the absence of known adverse treatment effects, allows for consideration of early and preventative treatment, liberal application and retreatment as necessary. The reset theory also suggests that the invention may have application to many different types of RPE-mediated retinal disorders. In fact, the inventor has recently shown that panmacular treatment can significantly improve retinal function and health, retinal sensitivity, and dynamic log MAR visual acuity and contrast visual acuity in dry age-related macular degeneration, retinitis pigmentosa, cone-rod retinal degenerations, and Stargardt's disease where no other treatment has previously been found to do so.

Currently, retinal imaging and visual acuity testing guide management of chronic, progressive retinal diseases. As tissue and/or organ structural damage and vision loss are late disease manifestations, treatment instituted at this point must be intensive, often prolonged and expensive, and frequently fails to improve visual acuity and rarely restores normal vision. As the invention has been shown to be an effective treatment for a number of retinal disorders without adverse treatment effects, and by virtue of its safety and effectiveness, it can also be used to treat an eye to stop or delay the onset or symptoms of retinal disorders prophylactically or as a preventative treatment for such retinal diseases. Any treatment that improves retinal function, and thus health, should also reduce disease or disorder severity, progression, untoward events and visual loss. By beginning treatment early, prior to pathologic structural change, and maintaining the treatment benefit by regular functionally-guided re-treatment, structural degeneration and visual loss might thus be delayed if not prevented. Even modest early reductions in the rate of disease or disorder progression may lead to significant long-term reductions and complications in visual loss. By mitigating the consequences of the primary defect, the course of disease may be muted, progression slowed, and complications and visual loss reduced. This is reflected in the inventor's studies, finding that treatment reduces the risk of progression and visual loss in diabetic retinopathy by 85% and AMD by 80%.

As SDM has been successfully used in homeotrophy or "reset to default" by normalizing the function of the RPE, retinal function and autoregulation and the biological function of the RPE, it is believed that application of SDM can restore normal retinal physiology and autoregulation as well to slow, stop or even reverse the progression of myopia, and particularly pediatric myopia in the same way that it does other chronic progressive retinopathies.

A laser light beam, that is sublethal and creates true subthreshold photocoagulation or photostimulation of retinal tissue, is generated and at least a portion of the retinal tissue is exposed to the generated laser light beam without damaging the exposed retinal or foveal tissue, so as to provide preventative and protective treatment of the retinal tissue of the eye. The treated retina may comprise the fovea, foveola, retinal pigment epithelium (RPE), choroid, choroidal neovascular membrane, subretinal fluid, macula, macular edema, parafovea, and/or perifovea. The laser light beam may be exposed to only a portion of the retina, or substantially the entire retina and fovea, or other eye tissue. This procedure is applied to tissue of the eye, such as retinal and/or foveal tissue, of an eye having myopia or a risk of having myopia.

While most treatment effects appear to be long-lasting, if not permanent, clinical observations suggest that it can appear to wear off on occasion. Accordingly, the retina is periodically retreated. This may be done according to a set schedule or when it is determined that the retina of the patient is to be retreated, such as by periodically monitoring visual and/or retinal function or condition of the patient.

Although several embodiments have been described in detail for purposes of illustration, various modifications may be made without departing from the scope and spirit of the invention. Accordingly, the invention is not to be limited, except as by the appended claims.

What is claimed is:

1. A process for treating myopia, comprising the steps of:
   providing a pulsed energy source having energy parameters including wavelength or frequency, duty cycle and pulse train duration, the energy parameters selected so as to achieve a therapeutic or prophylactic effect while not permanently damage eye tissue;
   determining that an eye has myopia and
   applying the pulsed energy to retinal and/or foveal tissue of the eye determined to have myopia to stimulate heat shock protein activation in the eye tissue;
   wherein the pulsed energy is applied to a plurality of eye tissue areas, and wherein adjacent pulsed energy treated eye tissue areas are separated by at least a predetermined distance to avoid thermal tissue damage; and wherein the pulsed energy comprises a pulsed light beam having a wavelength between 530 nm to 1300 nm, a duty cycle of less than 10%, and a pulse train duration between 0.1 and 0.6 seconds.

2. The process of claim 1, wherein the applying step includes the step of raising the eye tissue temperature between six degrees Celsius to eleven degrees Celsius at least during application of the pulsed energy source while maintaining an average eye tissue temperature over several minutes below a predetermined level.

3. The process of claim 2, wherein the total temperature increase of the eye tissue is maintained at approximately one degree Celsius or less over several minutes.

4. The process of claim 3, wherein the total temperature increase of the eye tissue is maintained at one degree Celsius or less over a six minute period of time.

5. The process of claim 1, wherein the pulsed energy is applied to a first eye tissue area and, after a predetermined period of time within a single treatment session, the pulsed energy is reapplied to the first eye tissue area, and during an interval between pulsed energy applications to the first eye tissue area the pulsed energy is applied to a second eye tissue area.

6. The process of claim 1, wherein the pulsed light beam has a duty cycle between 2.5% and 5%, a wavelength between 880 nm and 1000 nm.

7. The process of claim 6, wherein the pulsed light beam has a power between 0.5 and 74 watts.

8. A process for treating myopia, comprising the steps of:
providing a pulsed energy source having energy parameters including wavelength or frequency, duty cycle and pulse train duration, the energy parameters selected so as to achieve a therapeutic or prophylactic effect while not permanently damage eye tissue;
determining that an eye has myopia; and
applying the pulsed energy to retinal tissue, including at least a portion of the fovea, of the eye determined to have myopia to stimulate heat shock protein activation in the eye tissue;
wherein the pulsed energy comprises a pulsed light beam having a wavelength between 530 nm to 1300 nm, a duty cycle of less than 10%, and a pulse train duration between 0.1 and 0.6 seconds.

9. The process of claim 8, wherein the pulsed light beam has a duty cycle between 2.5% and 5%, a wavelength between 880 nm and 1000 nm.

10. The process of claim 9, wherein the pulsed light beam has a power between 0.5 and 74 watts.

11. The process of claim 8, wherein the pulsed energy is applied to a first eye tissue area and, after a predetermined period of time within a single treatment session, the pulsed energy is reapplied to the first eye tissue area, and during an interval between pulsed energy applications to the first eye tissue area the pulsed energy is applied to a second eye tissue area.

12. The process of claim 11, wherein the pulsed energy is applied to a plurality of eye tissue areas, and wherein adjacent pulsed energy treated eye tissue areas are separated by at least a predetermined distance to avoid thermal tissue damage.

13. The process of claim 11, wherein the applying step includes the step of raising the eye tissue temperature between six degrees Celsius to eleven degrees Celsius at least during application of the pulsed energy source while maintaining an average eye tissue temperature over several minutes below a predetermined level.

14. The process of claim 13, wherein the total temperature increase of the eye tissue is maintained at approximately one degree Celsius or less over several minutes.

15. The process of claim 14, wherein the total temperature increase of the eye tissue is maintained at one degree Celsius or less over a six minute period of time.

16. A process for treating myopia, comprising the steps of:
providing a pulsed light beam having energy parameters, including a wavelength between 530 nm to 1300 nm, a duty cycle of less than 10%, and a pulse train duration between 0.1 and 0.6 seconds, selected so as to achieve a therapeutic or prophylactic effect while not permanently damage eye tissue;
determining that an eye has myopia or is at a risk of having myopia; and
applying the pulsed light beam to retinal and/or foveal tissue of the eye determined to have myopia to raise eye tissue temperature between six degree Celsius to eleven degrees Celsius at least during application of the pulsed light beam to stimulate heat shock protein activation in the eye tissue while maintaining a total temperature increase of the eye tissue over a time period of six minutes from the application of the pulsed light beam to the eye tissue to one degree Celsius or less so as to not permanently damage the eye tissue;
wherein the pulsed light beam is applied to a plurality of eye tissue areas, and wherein adjacent pulsed energy treated eye tissue areas are separated by at least a predetermined distance to avoid thermal tissue damage.

17. The process of claim 16, wherein the pulsed light beam is applied to a first eye tissue area and, after a predetermined period of time within a single treatment session, the pulsed light beam is reapplied to the first eye tissue area, and during an interval between pulsed light beam applications to the first eye tissue area the pulsed light beam is applied to a second eye tissue area.

18. The process of claim 16, wherein the pulsed light beam has a duty cycle between 2.5% and 5%, a wavelength between 880 nm and 1000 nm.

19. The process of claim 18, wherein the pulsed light beam has a power between 0.5 and 74 watts.

20. The process of claim 1, wherein a plurality of pulsed energy treatment light beams are simultaneously applied to the retinal tissue.

21. The process of claim 1, wherein the pulsed energy is applied to substantially the entire retina, including the fovea, of the eye.

22. The process of claim 16, wherein a plurality of pulsed energy treatment beams are simultaneously applied to the retinal tissue.

23. The process of claim 16, wherein the pulsed energy is applied to substantially the entire retina, including the fovea, of the eye.

24. The process of claim 5, wherein the pulsed energy is applied to the second eye tissue area between pulses applied to the first tissue area, and the pulsed energy is returned and reapplied to the first eye tissue area in less than one second.

25. The process of claim 17, wherein the pulsed energy is applied to the second eye tissue area between pulses applied to the first tissue area, and the pulsed energy is returned and reapplied to the first eye tissue area in less than one second.

* * * * *